(12) United States Patent
Taintor

(10) Patent No.: US 7,262,021 B1
(45) Date of Patent: Aug. 28, 2007

(54) METHOD FOR ANTIMICROBIAL SUSCEPTIBILITY TESTING OF MICROORGANISMS

(76) Inventor: Read Taintor, 98 Mason La., North Salt Lake, UT (US) 84054

(*) Notice: Subject to any disclaimer, the term of this patent is extended or adjusted under 35 U.S.C. 154(b) by 158 days.

(21) Appl. No.: 11/028,155

(22) Filed: Jan. 3, 2005

Related U.S. Application Data

(63) Continuation-in-part of application No. 10/036,042, filed on Nov. 9, 2001, now abandoned.

(51) Int. Cl.
| | | |
|---|---|---|
| *C12Q 1/00* | (2006.01) | |
| *C12Q 1/04* | (2006.01) | |
| *C12Q 1/08* | (2006.01) | |
| *C12Q 1/20* | (2006.01) | |
| *C12N 1/24* | (2006.01) | |
| *C12N 1/00* | (2006.01) | |
| *C12N 1/20* | (2006.01) | |

(52) U.S. Cl. .............................. 435/33; 435/4; 435/30; 435/34; 435/40; 435/243

(58) Field of Classification Search ...................... None
See application file for complete search history.

(56) References Cited

U.S. PATENT DOCUMENTS

| | | | |
|---|---|---|---|
| 3,715,280 A | 2/1973 | Farmer, III | |
| 4,090,920 A | 5/1978 | Studer, Jr. | |
| 4,275,154 A | 6/1981 | Hall | |
| 4,448,534 A * | 5/1984 | Wertz et al. ................. | 356/435 |
| 4,701,850 A | 10/1987 | Gibbs | |
| 5,336,600 A | 8/1994 | Monget | |
| 5,344,761 A | 9/1994 | Citri | |
| 5,464,755 A | 11/1995 | Bochner | |
| 5,501,959 A * | 3/1996 | Lancaster et al. .............. | 435/32 |
| 5,627,045 A | 5/1997 | Bochner et al. | |
| 5,789,191 A | 8/1998 | Mayer et al. | |
| 5,882,882 A | 3/1999 | Bochner et al. | |
| 5,922,593 A | 7/1999 | Livingston | |
| 5,989,851 A | 11/1999 | Self et al. | |
| 5,998,214 A | 12/1999 | Guirguis | |
| 6,010,896 A | 1/2000 | Eisenberg et al. | |
| 6,015,941 A | 1/2000 | Rao | |
| 6,046,021 A | 4/2000 | Bochner | |
| 6,130,057 A | 10/2000 | Gosnell et al. | |
| 6,153,400 A | 11/2000 | Matsumura et al. | |
| 6,159,719 A | 12/2000 | Laine et al. | |
| 6,251,624 B1 | 6/2001 | Matsumura et al. | |
| 6,258,526 B1 * | 7/2001 | Stein et al. ..................... | 435/4 |
| 6,271,001 B1 | 8/2001 | Clarke et al. | |
| 6,280,928 B1 | 8/2001 | Scholl et al. | |
| 6,387,651 B1 | 5/2002 | Bochner et al. | |
| 6,416,969 B2 * | 7/2002 | Matsumura et al. .......... | 435/32 |

OTHER PUBLICATIONS

Webpage, Details of Carrageenan, 2 pages, Jul. 31, 2003.
Webpage, Carrageenan information, 2 pages, Jul. 31, 2003.
Webpage, Product Information, Carrageenan, 1 page, Jul. 31, 2003.
Webpage, Carrageenans, 5 pages, Oct. 19, 2001.
Webpage, GENU Carrageenan, 12 pages, Jul. 31, 2003.
Webpage, "Carrageenan: Technical Information," CEAMSA, 3 pages, Sep. 8, 2001.
Webpage, Definitions, 10 pages, Oct. 1, 2003.
Webpage, FMC Marine Colloids-Carrageenan, FMC BioPolymer, 3 pages, Oct. 1, 2003.
Webpage, Introduction to Natural Grade Carrageenan, 8 pages, Jul. 31, 2003.
The Tic Times, Winter 2002, 4 pages.
Abbott, IA, et al., "Evaluation of Kappa Carrageenan as a Substitute for Agar in Microbiological Media," Arch. Microbiol. 1981 Feb. 128 (4) 355-359.
Astier-Gin et al., "Identification of HTLV-1 or HTLV-II-Producing Cells by Cocultivation with BHK-21 Cells Stably Transfected with a LTR-lacZ Gene Construct," J. Virological Methods 51:19-30, Jun. 20, 1994.
Dagan, et al., "A Combination of Four Cell Types for Rapid Detection of Enteroviruses in Clinical Specimens," J. Med, Virol 19: 219-229 (1986).
Lines, AD, "Value of the K+ Salt of Carageenan as an Agar Substitute in Routine Bacteriological Media," Appl. Environ. Microbiol, Dec. 1997; 34 (6) 637-9.
Pittman KA, et al., "Carrageenan: the Effect of Molecular Weight and Polymer Type on its Uptake, Excretion and Degradation in Animals," Food Cosmet Toxicol. Apr. 14, 1976 (2) 85-93.
Rabalais et al., "Rapid Diagnosis of Respiratory Viral Infection by Using a Shell Vial Assay and Monoclonal Antibody Pool," J. Clin. Microbiol. 30:1505-1508 (1992).
Rodriguez, A.I., et al., "Dynamic viscoelastic behavior of gellan-t-carrageenan and gellan-xanthan gels," Food Hydrocolloids, 13 (1999) 59-64.
Watson, N, et al., "Substitute for Agar in Solid Media for Common Usages in Microbiology," Appl. Environ. Microbiol, Apr. 31, 1976 (4) 509-13.

* cited by examiner

*Primary Examiner*—David M. Naff
*Assistant Examiner*—Deborah K. Ware
(74) *Attorney, Agent, or Firm*—Kirton & McConkie; Evan R. Witt

(57) ABSTRACT

Media, kits, and methods are disclosed for use in processes requiring microbial culture. More specifically, the invention provides carrageenan-stabilized agar-based microbial culture media for kits and methods. The media and kits of the invention possess increased shelf-life stability over currently available agar-based media. Further, the media, kits, and methods are useful in the manual determination of identification and antimicrobial susceptibility testing of the pathogen/s contained in a specimen or sample in periods of about 12 to 24 hours. The stabilized culture media of the invention are useful in a broad variety of applications.

11 Claims, 18 Drawing Sheets

(10 of 18 Drawing Sheet(s) Filed in Color)

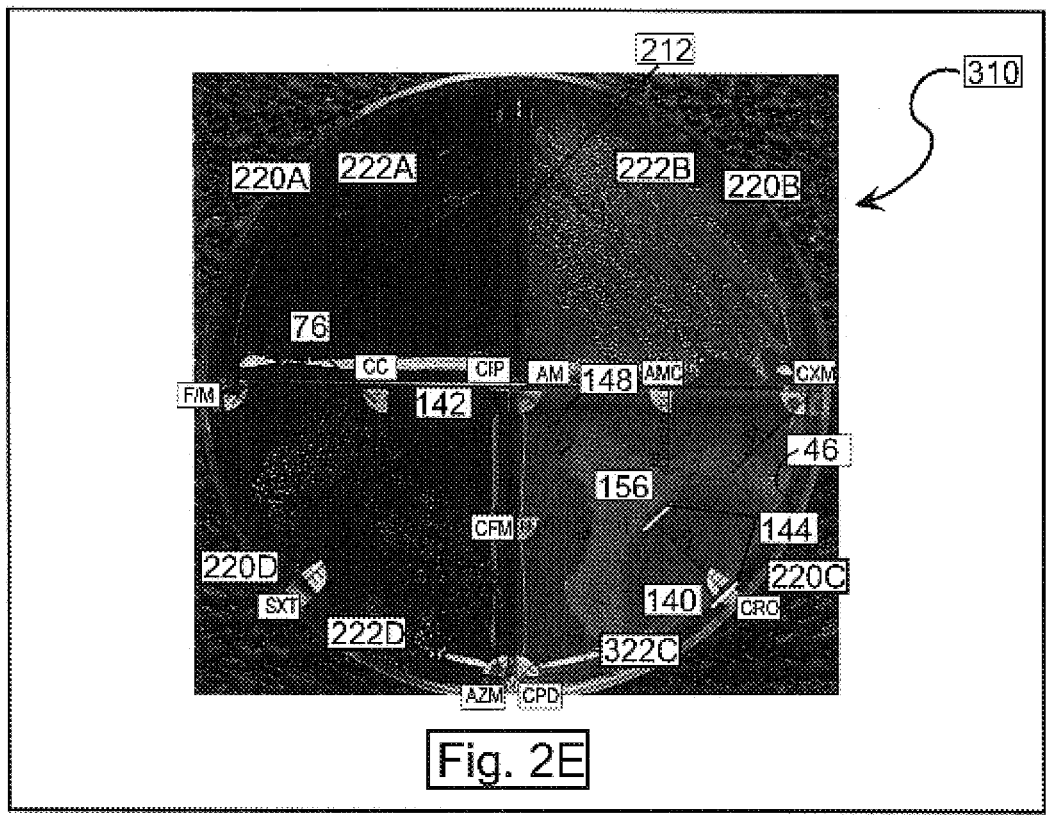

Fig. 2E

Comparison of Standard Kirby Bauer assay(Fig.2C) to quarter of Kirby Bauer antimicrobial disk placed on edge of dish(Fig. 2D) to embodiment using Kirby Bauer disk quarters(Fig.2E)

Measurement (mm) following 18hr. incubation with E.coli

| Anti-microbial | Standard Kirby-B. Fig. 2C | Quarter at edge Fig. 2D | Quarter used with IDSX Fig2E |
|---|---|---|---|
| code | diameter | radius | radius |
| AM | 20 | 9 | 9 |
| AMC | 20 | 9 | 9 |
| AZM | 13 | 6 | 7 |
| CFM | 23 | 11.5 | 10.5 |
| CPD | 23 | 11.5 | 11 |
| CXM | 23 | 11.5 | 11 |
| CC | 6 | 3 | 3 |
| CIP | 28 | 14 | 14 |
| CRO | 30 | 15 | 13.5 |
| F/M | 19 | 9.5 | 10 |
| SXT | 27 | 12 | 13 |

Fig. 2F

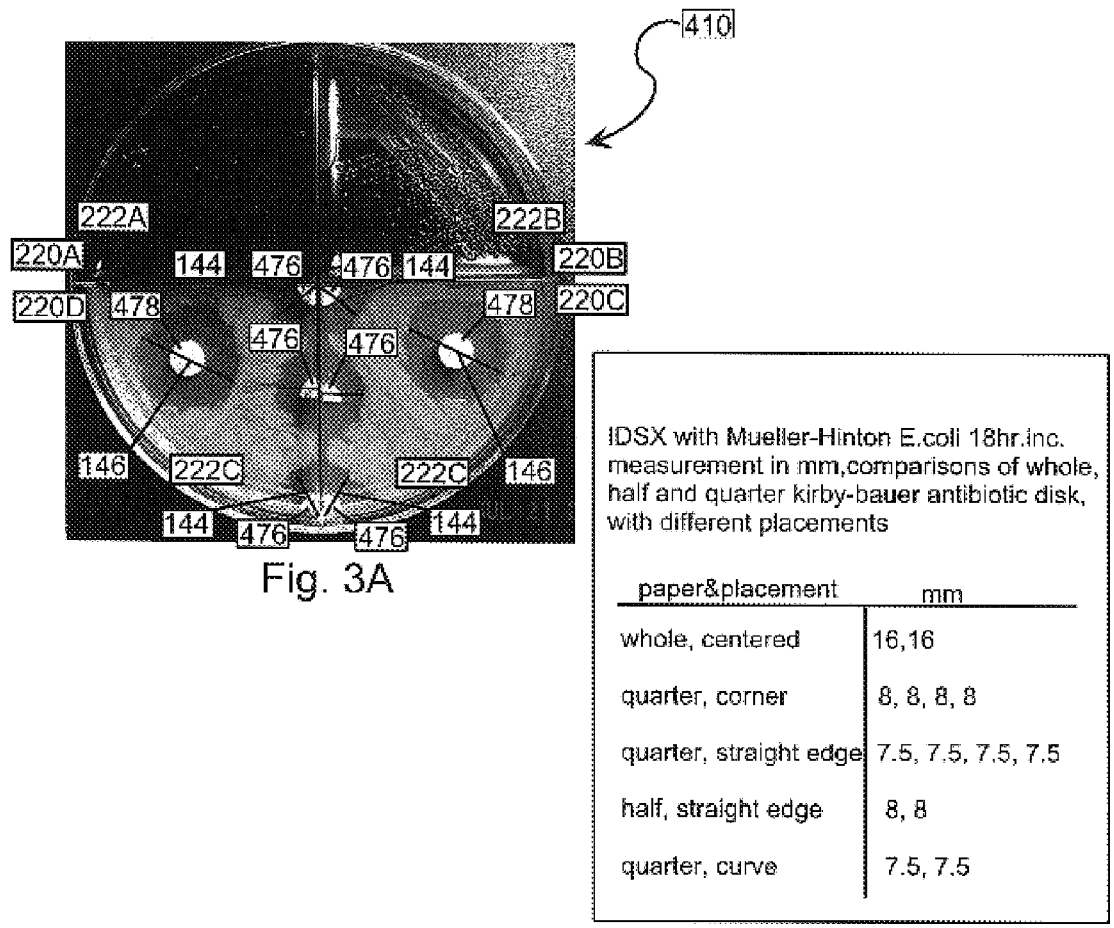
Fig. 3A
Fig. 3C
IDSX with Mueller-Hinton E.coli 18hr.inc. measurement in mm, comparisons of whole, half and quarter kirby-bauer antibiotic disk, with different placements
| paper&placement | mm |
|---|---|
| whole, centered | 16,16 |
| quarter, corner | 8, 8, 8, 8 |
| quarter, straight edge | 7.5, 7.5, 7.5, 7.5 |
| half, straight edge | 8, 8 |
| quarter, curve | 7.5, 7.5 |
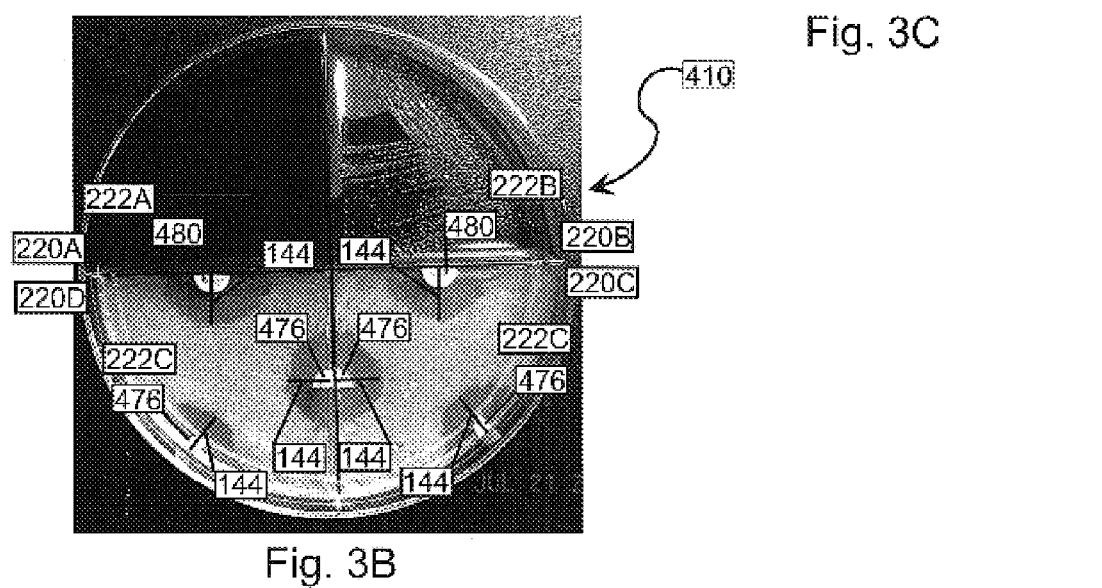
Fig. 3B

TABLE OF COLONY CHARACTERISTICS USED IN KIT INVENTION

ELEVATIONS: FLAT, RAISED, PULVINATE, CONVEX, UMBONATE, UMBILICATE

MARGINS: ENTIRE, UNDULATE, CURLED, FILAMENTOUS

| | |
|---|---|
| FORM:<br>OVERALL SHAPE OF COLONY WHEN VIEWED FROM TOP | CIRCULAR - MOSTLY ROUND, MAY BE SLIGHTLY UNEVEN<br>WRINKLED UNEVEN SURFACE TEXTURE, OFTEN DRY IN APPEARANCE<br>IRREGULAR - EDGES VERY UNEVEN<br>RHIZOIDAL - BRANCHED (UNCOMMON)<br>FILAMENTOUS - POWDERY, SPREADING LINES (FUNGI)<br>CURLED - SEPARATED EDGES, CONCENTRIC CIRCLES (UNCOMMON) |
| ELEVATION:<br>VIEW COLONY FROM SIDE | FLAT - WHEN LIGHT IS REFLECTED ACROSS SURFACE OF COLONY, NO CONVEX SHAPE IS SEEN (COMMON)<br>RAISED - ELEVATED (COMMON)<br>CONVEX - SLIGHT DOME SHAPE (COMMON)<br>PULVINATE - HAT-LIKE APPEARANCE -DOMED IN MIDDLE, SLIGHTLY RAISED AT EDGES (MOST SIGNIFICANT IN 1-2 DAY CULTURE |
| MARGIN:<br>VIEW EDGE OF COLONY | ENTIRE - SMOOTHLY CURVING EDGE (COMMON)<br>UNDULATE - WAVY EDGE (COMMON)<br>LOBATE - VERY IRREGULAR AMOEBA-LIKE EDGES (UNCOMMON)<br>FILAMENTOUS - POWDERY LINES (FUNGI)<br>CURLED - SEPARATE EDGES (UNCOMMON) |
| CONSISTENCY:<br>TEXTURE OF COLONY WHEN LOOP IS INSERTED INTO IT | BUTYROUS - BUTTER-LIKE, CAN PICK US PASTE EASILY<br>MUCOID - SLIMY (<3MM OF SLIME THAT ATTACHES TO END OF LOOP WHEN SAMPLING) (COMMON)<br>VISCID- STICKY, RESISTANT TO PICK UP OF PASTE, SOME ELASTICITY OF COLONY HAS BEEN LOST (UNCOMMON)<br>WAXLIKE - COLONY FRAGMENTS WHEN BEING PICKED UP (UNCOMMON)<br>POWDERY - LIGHT FILAMENTS (FOUND MOSTLY IN MOLDS) |
| PIGMENT (COLOR) | OFF-WHITE - ANY VARIATION ON WHITE, INCLUDING GREY, TAN, CREAM, IVORY VERY PALE YELLOW<br>WHITE - PORCELAIN WHITE ONLY (UNCOMMON) |
| APPEARANCE (REFLECTED LIGHT) | TEXTURE AS YOU TILT PLATE AND VIEW AT AN ANGLE FROM THE TOP UNDER A BRIGHT LIGHT |
| APPEARANCE (TRANSMITTED LIGHT) VIEW WHILE HOLDING UP TO BRIGHT LIGHT AND LOOK THROUGH COLONIES. | TRANSPARENT - COMPLETELY SEE-THROUGH, COLONIES HARD TO SEE (UNCOMMON).<br>TRANSLUCENT - CAN SEE MODEST REDUCTION OF LIGHT PASSING THROUGH COLONY (COMMON)<br>OPAQUE - ALMOST NO LIGHT PASSES THROUGH COLONY (COMMON) |
| DIAMETER OF COLONY | COLONIES NEED TO BE WELL SEPARATED. FUNCTION OF TIME |
| EFFECT OF THE COLONY ON CULTURE MEDIUM | ACTION OF THE COLONY ON THE SURROUNDING MEDIUM: HEMOLYTIC REACTIONS, COLOR AND OTHER REACTIONS DUE TO THE CHEMISTRY OF THE GROWTH MEDIUM |

Fig. 9

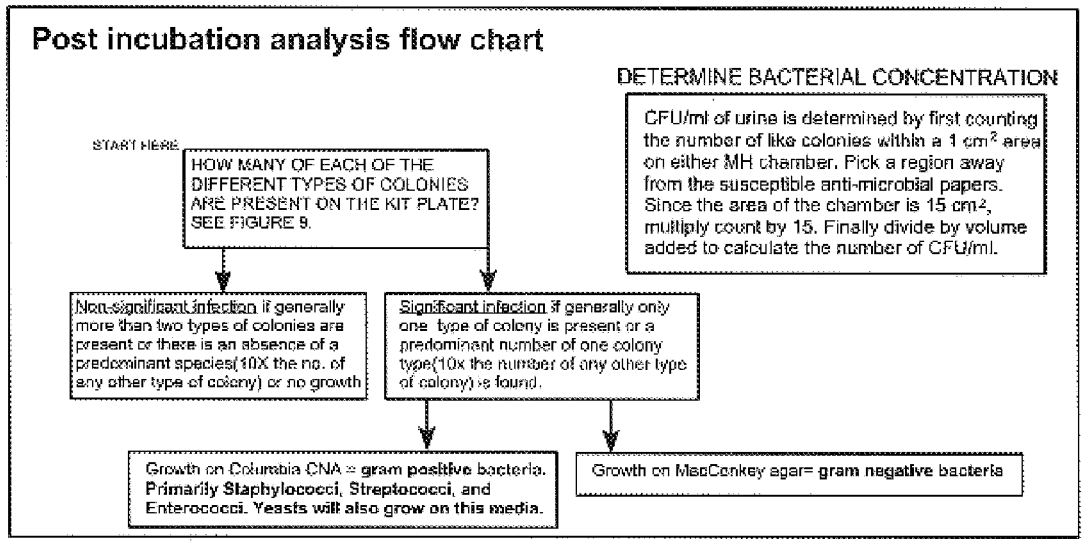
Fig. 10
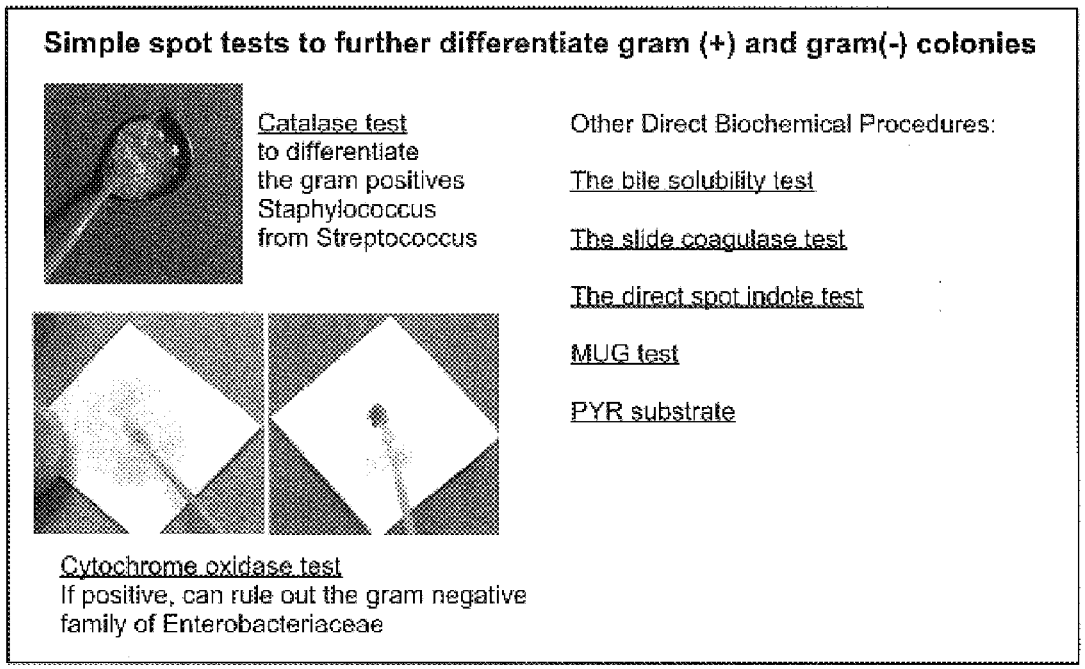
Fig. 11, Prior Art

TABLE OF CELLULAR MORPHOLOGY BY LIGHT
MICROSCOPE OBSERVATION (400X-600X).
MOTILITY MAY BE OBSERVED WITH SOME OF THESE.

| 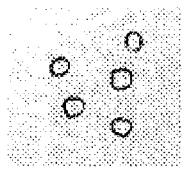 Spherical cells (COCCI) |  Rod-shaped cells (BACILLI) | 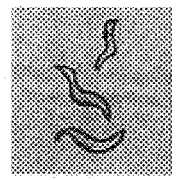 Spiral-shaped cells (SPIRILLA) |
|---|---|---|
| 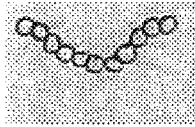 Streptococci | 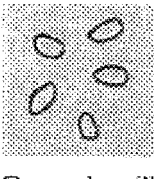 Coccobacilli (short rods) | 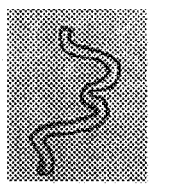 Borrelia-type spirillum |
| 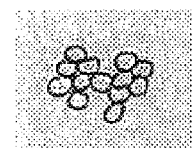 Staphylococci | 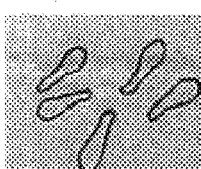 Coryneform bacilli (club shaped rods) | 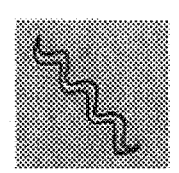 Treponema-type spirillum |
| 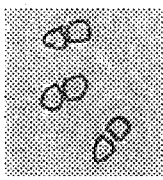 Diplococci | 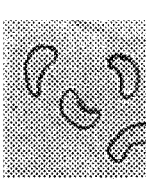 Vibrio (comma shaped rods) | 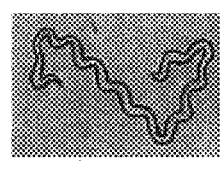 Leptospira-type spirillum |

Fig. 12

| TABLE I---INTERPRETATIVE STANDARDS TABLE ||||||
|---|---|---|---|---|---|
| Antimicrobial agent || Color | Zone radius |||
| generic name | trade name || Compare to value below for R,I or S |||
| | | | Resistant | Intermediate | Susceptible |
| Ampicillin | Omnipen, Polycillin | orange | ≤ 5.5 | 6-6.5 | ≥ 7 |
| | | | gram neg. enteric & enterococci |||
| | | | ≤ 10 | 10.5-14 | ≥ 14.5 |
| | | | staph.& pen.G susceptible organisms |||
| Amoxicillin/Clavulanate | Augmentin | green | ≤ 6.5 | 7-8.5 | ≥ 9 |
| | | | gram neg. enteric & enterococci |||
| | | | ≤ 9.5 | - | ≥ 10 |
| | | | staph.& pen.G susceptible organisms |||
| Cephalothin,Cephapirin, Cephradine,Cephalexin, Cefaclor,Cefadroxil | Cefadyl, Velocef,Keflex Ceclor,Duricef | violet | ≤ 7 | 7.5-8.5 | ≥ 9 |
| Ciprofloxicin | Cipro | black | ≤ 7.5 | 8-10 | ≥ 10.5 |
| Doxycycline | Vibramycin | yellow | ≤ 6 | 6.5-7.5 | ≥ 8 |
| Erythromycin | Iotycin | red | ≤ 7.5 | 8-11 | ≥ 11.5 |
| Levofloxicin | Levaquin | brown | ≤ 6.5 | 7-8 | ≥ 8.5 |
| Trimethoprim/Sulfamethoxazole | Septra, Bactrim | white | ≤ 5 | 5.5-7.5 | ≥ 8 |
| Nitrofurantoin | Macrobid, Macrodantin | black dot | ≤ 7 | 7.5-8 | ≥ 8.5 |

Fig. 13

| ZONE INTERPRETIVE CHART | | | ZONE RADIUS | | | ZONE DIAMETER | | |
|---|---|---|---|---|---|---|---|---|
| | | | Interpretive standards (mm) | | | Interpretive standards (mm) | | |
| ANTIMICROBIAL | | | R | I | S | R | I | S |
| AGENT | CODE | GROWTH ON: | ≤ | range | ≥ | ≤ | range | ≥ |
| amdinocillin | AMD | mac | 7.5 | - | 8 | 15 | - | 16 |
| amikacin | AN | mac or ccna | 7 | 7.5-8 | 8.5 | 14 | 15-16 | 17 |
| amoxicillin/ | AMC | mac | 6.5 | 7-8.5 | 9 | 13 | 14-17 | 18 |
| clavulanic acid | | ccna | 9.5 | - | 10 | 19 | - | 20 |
| ampicillin | AM | mac | 6.5 | 7-8 | 8.5 | 13 | 14-16 | 17 |
| | | ccna-staph. | 14 | - | 14.5 | 28 | - | 29 |
| | | ccna-other | 8 | - | 8.5 | 16 | - | 17 |
| ampicillin/ | SAM | mac or ccna | 5.5 | 6-7 | 7.5 | 11 | 12-14 | 15 |
| sulbactam | | | | | | | | |
| azithromycin | AZM | ccna | 6.5 | 7-8.5 | 9 | 13 | 14-17 | 18 |
| azlocillin | AZ | mac | 8.5 | - | 9 | 17 | - | 18 |
| aztreonam | ATM | mac | 7.5 | 8-10.5 | 11 | 15 | 16-21 | 22 |
| carbenicillin | CB | mac | 9.5 | 10-11 | 11.5 | 19 | 20-22 | 23 |
| cefaclor | CEC | mac or ccna | 7 | 7.5-8.5 | 9 | 14 | 15-17 | 18 |
| cefamandole | MA | mac or ccna | 7 | 7.5-8.5 | 9 | 14 | 15-17 | 18 |
| cefazolin | CZ | mac or ccna | 7 | 7.5-8.5 | 9 | 14 | 15-17 | 18 |
| cefdinir | CDR | mac or ccna | 8 | 7.5-9.5 | 10 | 16 | 17-19 | 20 |
| cefepime | FEP | mac or ccna | 7 | 7.5-8.5 | 9 | 14 | 15-17 | 18 |
| cefixime | CFM | mac | 7.5 | 8-9 | 9.5 | 15 | 16-18 | 19 |
| cefmetazole | CMZ | mac or ccna | 6 | 6.5-7.5 | 8 | 12 | 13-15 | 16 |
| cefonicid | CID | mac or ccna | 7 | 7.5-8.5 | 9 | 14 | 15-17 | 18 |
| cefoperazone | CFP | mac or ccna | 7.5 | 8-10 | 10.5 | 15 | 16-20 | 21 |
| cefotaxime | CTX | mac or ccna | 7 | 7.5-11 | 11.5 | 14 | 15-22 | 23 |
| cefotetan | CTT | mac or ccna | 6 | 6.5-7.5 | 8 | 12 | 13-15 | 16 |
| cefoxitin | FOX | mac or ccna | 7 | 7.5-8.5 | 9 | 14 | 15-17 | 18 |
| cefpodoxime | CPD | mac or ccna | 8.5 | 9-10 | 10.5 | 17 | 18-20 | 21 |
| cefprozil | CPR | mac or ccna | 7 | 7.5-8.5 | 9 | 14 | 15-17 | 18 |
| ceftazidime | CAZ | mac or ccna | 7 | 7.5-8.5 | 9 | 14 | 15-17 | 18 |
| ceftibuten | CTB | mac | 8.5 | 9-10 | 10.5 | 17 | 18-20 | 21 |
| ceftizoxime | ZOX | mac or ccna | 7 | 7.5-9.5 | 10 | 14 | 15-19 | 20 |
| ceftriaxone | CRO | mac or ccna | 6.5 | 7-10 | 10.5 | 13 | 14-20 | 21 |
| cefuroxime | CXM | mac or ccna | 7 | 7.5-8.5 | 9 | 14 | 15-17 | 18 |
| cephalothin | CF | mac or ccna | 7 | 7.5-8.5 | 9 | 14 | 15-17 | 18 |
| chloramphenicol | C | mac or ccna | 6 | 6.5-8.5 | 9 | 12 | 13-17 | 18 |
| cinoxacin | CIN | mac | 7 | 7.5-9 | 9.5 | 14 | 15-18 | 19 |
| ciprofloxacin | CIP | mac or ccna | 7.5 | 8-10 | 10.5 | 15 | 16-20 | 21 |
| clarithromycin | CLR | ccna | 8 | 8.5-10 | 10.5 | 16 | 17-20 | 21 |
| clindamycin | CC | ccna | 7 | 7.5-10 | 10.5 | 14 | 15-20 | 21 |
| colistin | CL | mac or ccna | 4 | | 5.5 | 8 | 9-10 | 11 |
| doxycycline | D | mac or ccna | 6 | 6.5-7.5 | 8 | 12 | 13-15 | 16 |
| enoxacin | ENX | mac or ccna | 7 | 7.5-8.5 | 9 | 14 | 15-17 | 18 |
| erythromycin | E | ccna | 6.5 | 7-11 | 11.5 | 13 | 14-22 | 23 |
| fosfomycin | FOS | mac or ccna | 6 | 6.5-7.5 | 8 | 12 | 13-15 | 16 |
| | | E.coli & E. faecalis only | | | | | | |
| gatifloxacin | GAT | mac or ccna | 7 | 7.5-8.5 | 9 | 14 | 15-17 | 18 |
| gentamicin | GM | mac or ccna | 6 | 6.5-7 | 7.5 | 12 | 13-14 | 15 |

Fig. 14A

| ZONE INTERPRETIVE CHART | | | ZONE RADIUS | | | ZONE DIAMETER | | |
|---|---|---|---|---|---|---|---|---|
| | | | Interpretive standards (mm) | | | Interpretive standards (mm) | | |
| ANTIMICROBIAL | | | R | I | S | R | I | S |
| AGENT | CODE | GROWTH ON: | ≤ | range | ≥ | ≤ | range | ≥ |
| grepafloxacin | GRX | mac or ccna | 7 | 7.5-8.5 | 9 | 14 | 15-17 | 18 |
| imipenem | IPM | mac or ccna | 6.5 | 7-7.5 | 8 | 13 | 14-15 | 16 |
| kanamycin | K | mac or ccna | 6.5 | 7-8.5 | 9 | 13 | 14-17 | 18 |
| levofloxacin | LVX | mac or ccna | 6.5 | 7-8 | 8.5 | 13 | 14-16 | 17 |
| linezolid | LZD | ccna | 10 | 10.5-11 | 11.5 | 20 | 21-22 | 23 |
| lomefloxacin | LOM | mac or ccna | 9 | 9.5-10.5 | 11 | 18 | 19-21 | 22 |
| loracarbef | LOR | ccna | 7 | 7.5-8.5 | 9 | 14 | 15-17 | 18 |
| meropenem | MEM | mac or ccna | 6.5 | 7-7.5 | 8 | 13 | 14-15 | 16 |
| mezlocillin | MZ | mac | 8.5 | 9-10 | 10.5 | 17 | 18-20 | 21 |
| minocycline | MI | mac or ccna | 7 | 7.5-9 | 9.5 | 14 | 15-18 | 19 |
| moxalactam | MOX | mac or ccna | 7 | 7.5-11 | 11.5 | 14 | 15-22 | 23 |
| moxifloxacin | MXF | mac or ccna | 7.5 | 8-9 | 9.5 | 15 | 16-18 | 19 |
| nafcillin | NF | ccna, staph A | 5 | 5.5-6 | 6.5 | 10 | 11-12 | 13 |
| nalidixic acid | NA | mac | 6.5 | 7-9 | 9.5 | 13 | 14-18 | 19 |
| neomycin | N | mac or ccna | 6 | 6.5-8 | 8.5 | 12 | 13-16 | 17 |
| netilmicin | NET | mac or ccna | 6 | 6.5-7 | 7.5 | 12 | 13-14 | 15 |
| nitrofurantoin | F/M | mac or ccna | 7 | 7.5-8 | 8.5 | 14 | 15-16 | 17 |
| norfloxacin | NOR | mac or ccna | 6 | 6.5-8 | 8.5 | 12 | 13-16 | 17 |
| novobiocin | NB | mac or ccna | 8.5 | 9-10.5 | 11 | 17 | 18-21 | 22 |
| ofloxacin | OFX | mac or ccna | 6 | 6.5-7.5 | 8 | 12 | 13-15 | 16 |
| oxacillin | OX | ccna | 8.5 | - | 9 | 17 | - | 18 |
| oxolinic acid | OA | mac or ccna | 5 | - | 5.5 | 10 | - | 11 |
| penicillin | P | ccna | 14 | - | 14.5 | 28 | - | 29 |
| piperacillin | PIP | mac | 8.5 | 9-10 | 10.5 | 17 | 18-20 | 21 |
| piperacillin/ tazobactam | TZP | mac | 8.5 | 9-10 | 10.5 | 17 | 18-20 | 21 |
| polymyxin B | PB | mac or ccna | 4 | 4.5-5.5 | 6 | 8 | 9-11 | 12 |
| quinupristin/ dalfopristin | SYN | mac or ccna | 7.5 | 8-9 | 9.5 | 15 | 16-18 | 19 |
| rifampin | RA | ccna | 8 | 8.5-9.5 | 10 | 16 | 17-19 | 20 |
| sparfloxacin | SPX | ccna | 7.5 | 8-9 | 9.5 | 15 | 16-18 | 19 |
| streptomycin | S | mac | 5.5 | 6-7 | 7.5 | 11 | 12-14 | 15 |
| sulfisoxazole | G | mac or ccna | 6 | 6.5-8 | 8.5 | 12 | 13-16 | 17 |
| tetracycline | TE | mac or ccna | 7 | 7.5-9 | 9.5 | 14 | 15-18 | 19 |
| ticarcillin | TIC | mac | 7 | 7.5-9.5 | 10 | 14 | 15-19 | 20 |
| ticarcillin/ clavulanic acid | TIM | mac ccna | 7 11 | 7.5-9.5 - | 10 11.5 | 14 22 | 15-19 - | 20 23 |
| tobramycin | NN | mac or ccna | 6 | 6.5-7 | 7.5 | 12 | 13-14 | 15 |
| trimethoprim | TMP | mac or ccna | 5 | 5.5-7.5 | 8 | 10 | 11-15 | 16 |
| trimethoprim/ sulfamethoxazole | SXT | mac or ccna | 5 | 5.5-7.5 | 8 | 10 | 11-15 | 16 |
| trovafloxacin | TVA | ccna | 7.5 | 8-9 | 9.5 | 15 | 16-18 | 19 |
| vancomycin | VA | ccna | 7 | 7.5-8 | 8.5 | 14 | 15-16 | 17 |

Fig. 14B

| Frequent Bacterial Isolates From Various Clinical Specimens | | |
|---|---|---|
| Specimen | Pathogens | Normal Flora |
| Blood | Staphylococci | None |
| | Enteric gram-negative bacilli | |
| | Streptococcus pneumoniae | |
| | Haemophilus influenzae | |
| | Nonfermentative gram-negative bacilli | |
| | Anaerobes | |
| | Neisseria meningitidis | |
| Closed cavity body fluids: CSF, synovial, pleural, pericardial, amniotic, etc. | Haemophilus influenzae | None |
| | Streptococcus pneumoniae | |
| | Enteric gram-negative bacilli | |
| | Staphylococci | |
| | Neisseria meningitidis | |
| Urine | Enteric gram-negative bacilli | None |
| | Enterococci | |
| | Staphylococcus saprophyticus | |
| | Nonfermentativew gram-negative bacilli | |
| Stool | Salmonella spp. | Anerobes, Nonpathogenic- enteric gram-negative- bacilli, Enterococci |
| | Campylobacter spp. | |
| | Shigella spp. | |
| | Enterohemorrhagic Escherichia coli | |
| | Clostridium difficile | |
| | Yersinia enterocolitica | |
| Upper respiratory tract | Streptococcus pyogenes | Viridans streptococci, Neisseria spp., Haemophilus spp., Corynebacterium spp. |
| | Streptococcus pneumoniae | |
| | Haemophilus influenzae | |
| | Moraxella catarrhalis | |
| | Staphylococcus aureus | |
| Lower respiratory tract | Streptococcus pneumoniae | None |
| | Staphylococcus aureus | |
| | Anaerobes | |
| | Enteric gram-negative bacilli | |
| | Pseudomonas aeruginosa | |
| | Chlamydia trachomatis | |
| Eye | Haemophilus influenzae | None |
| | Neisseria gonorrhoeae | |
| | Chlamydia trachomatis | |
| | Pseudomonas aeruginosa | |
| Middle ear | Streptococcus pneumoniae | Staphylococci |
| | Haemophilus influenzae | |
| | Moraxella catarrhalis | |
| | Streptococcus pyogenes | |
| | Anaerobes | |
| Outer ear | Pseudomonas aeruginosa | Corynebacterium spp. |
| Genital tract | Neisseria gonorrhoeae | Lactobacilli, Streptococci, Staphylococci, Anaerobes, Gardnerella vaginalis |
| | Treponema pallidum | |
| | Haemophilus ducreyi | |
| | Chlamydia trachomatis | |
| | Mobiluncus spp. | |
| Wound | Staphylococcus aureus | None |
| | Streptococcus pyogenes | |
| | Anaerobes | |
| | Enteric gram-negative bacilli | |
| Bone, tissue | Staphylococcus aureus | None |
| | Enteric gram-negative bacilli | |
| | Pseudomonas aeruginosa | |

Fig. 15

METHOD FOR ANTIMICROBIAL SUSCEPTIBILITY TESTING OF MICROORGANISMS

CROSS-REFERENCED RELATED APPLICATIONS

This application is a continuation-in-part of prior application Ser. No. 10/036,042, filed Nov. 9, 2001 now abandoned, entitled "Method and Kit for Rapid Concurrent Identification and Antimicrobial Susceptibility Testing of Microorganisms from Broth Culture," which is incorporated herein by reference.

BACKGROUND OF THE INVENTION

Throughout history, humanity has fallen victim to pandemics of cholera, plague, influenza, typhoid, tuberculosis and other infectious maladies so widespread that few people survived into what is now considered "middle age." As recently as the 19th century, the average life span in Europe and North America was about 50 years. It was a world in which the likelihood of dying prematurely from infectious diseases was as high as 40%, and where women routinely succumbed to infections during childbirth which are now easily curable by today's standards. In underdeveloped nations, the situation was even worse. Unfortunately, however, unlike many industrialized nations, medical conditions in many underdeveloped nations have never really improved. Indeed, in poorer nations today, infectious diseases, both major and seemingly minor, still contribute to premature death and to the ongoing misery of underprivileged populations.

The emergence of multi-resistant, or "antimicrobial agent-resistant" bacteria, has threatened the security of developed nations and further shaken the citizens of less-developed countries, and is now a worldwide concern. In many nations, antimicrobial agents are used indiscriminately, further contributing to the rise of antibiotic resistance in a variety of bacteria, including species of *Enterococcus, Staphylococcus, Pseudomonas*, and the Enterobacteriaceae family. The emergence of antibiotic-resistant organisms is very often a result of the over-use of broad-spectrum antimicrobial agents. There is also concern that inappropriate veterinary use of antimicrobial agents may lead to development of antibiotic resistant bacteria. In some cases, these bacteria could then, in turn, infect humans.

The diagnosis of infectious diseases has traditionally relied upon various microbiological culture methods to identify the organism responsible for an infection and then to determine the appropriate antimicrobial treatment for the patient. These methods continue to be important for analysis, despite recent advances in molecular and immunological diagnostics. While the development of rapid and automated methods has served to increase the efficiency of microbiological analysis, traditional quantitative culture methods remain critical for definitive diagnosis of infections. See, Baron & Finegold, Diagnostic Microbiology, 8th ed. C. V. Mosby, (1990), p. 253. Further, these traditional methods are even more valuable in countries unable to afford newer methods, such as automated identification and susceptibility-testing methods. In addition, many areas of the world are devoid of adequate clinical microbiology facilities capable of providing access to newer diagnostic methods. Indeed, in some cases, even traditional culture-based methods are only narrowly available.

Traditional culture-based diagnostic methods share a general set of method steps. A first group of these steps involves the collection and transport of a specimen. The specimen must be material from the actual infection site. Once collected, it is necessary to maintain the sample as near to its original state as possible with minimum deterioration. Transport systems often consist of a protective container, transport medium and a culture swab. A problem with the use of a holding or transport medium is that it may jeopardize the recovery of certain strains. A major task is to reduce the time delay between collection of specimens and inoculation onto microbiological culture media. The transport container is constructed to minimize hazards to specimen handlers. It is best to minimize adverse environmental conditions, such as rapid changes in pressure, exposure to extremes of heat and cold or excessive drying. The transport of fluid specimens to the laboratory must be done as quickly as possible. It is recommended that a 2-hour maximum time limit be imposed between collection and delivery of specimens to the laboratory. This limit poses a problem for specimens collected any distance from a clinical microbiology laboratory.

In addition to the above difficulties, under some conditions, traditional microbiological culture media suffer from several weaknesses. First, satisfactory microbiological culture media must generally contain many components to successfully support bacterial life. More specifically, satisfactory media must include available sources of water, vitamins, inorganic phosphate and sulfur, trace metals, carbon and nitrogen. These needs may be supplied from a number of sources. In addition, various media may include agents which selectively allow the growth of specific organisms while preventing the growth of others. Media may often include compounds that enhance the ability of a user to identify the bacteria growing thereon. The following is a list of common media constituents with their sources in parenthesis: (1) Amino-nitrogen (peptone, protein hydrolysate, infusions and extracts), (2) Growth factors (blood, serum, yeast extract or vitamins, NAD), (3) Energy sources (sugar, alcohols, and carbohydrates), (4) Buffer salts (Phosphates, acetates and citrates), (5) Mineral salts and metals (phosphate, sulfate, magnesium, calcium, iron), (6) Selective agents (chemicals, antimicrobials and dyes), (7) Indicator dyes (phenol red, neutral red), and (8) Solidifying agents (agar, gelatin, alginate, silica gel, etc.).

A selection of the appropriate solid culture media for microbiological test(s) is generally made according to the particular specimen type. Several hundred standard culture media are commercially available. Various culture media have been developed to serve specific purposes, including the identification of bacteria and antibiotic susceptibility testing. One medium used in antibiotic susceptibility testing is Mueller Hinton agar. The media used as identification testing media can generally be divided into five groups: enriched media, differential media, selective media, differential-selective media, and single purpose media. Enriched media have special additives to support pathogens having fastidious growth needs. Examples of enriched media include sheep blood agar and brain heart infusion broth. Differential media allows the differentiation of groups of microorganisms based on color changes of an indicator (sensitive to a property such as pH) in the culture medium that take place as a result of biochemical reactions associated with microorganism growth. Separating organisms that ferment the sugar lactose, for example, from those that do not, is one example of the utility of differential media.

Selective media support the growth of certain microorganisms of interest while suppressing the growth of others. Azide blood agar, Columbia CNA agar with blood and Phenylethanol agar are examples. Gram-positive organisms grow on these media whereas gram-negative organisms do not. Differential-selective media combine the characteristics of both selective media and differential media, thus allowing the selective growth and rapid differentiation of major groups of bacteria. These media are widely used in tests for gram-negative bacilli (rods). MacConkey and Hektoen media are examples. Single-purpose media isolate one specific type of microorganism. Bile esculin azide agar is an example of this media. *Enterococcus* and group D *streptococcus* grow and cause the formation of a dark brown or black complex in the agar.

In modern microbiology laboratories, every attempt is made to use well-trained personnel, working under close supervision, in the processing of specimens. Errors or misjudgments made during laboratory processing, such as improper choice of culture media, can negate all the expertise one may apply in later processing steps such as the reading and interpretation of cultures. Expert microbiologists may often be caught short in making definitive diagnoses because of the selection and use of inadequate or incorrect media in culturing a specimen.

The equipment required for the primary inoculation of specimens includes several microbiological agar-based media plates and a nichrome or platinum inoculating wire or loop. Plastic disposable loops are also available. Plates currently used in the field generally have a shelf life of from one to two months. Specimens are "streaked out" on the surface of the plates to spread the microorganisms across the surface of the solid culture medium. This results in isolated colonies.

As the isolated microorganisms grow on the solid medium, they form a mass called a colony. This mass of cells originated from a single cell and now may consist of hundreds of thousands of cells. These colonies have distinct characteristics that are a clue in the process of identifying the microorganism (see FIG. 9). The microscopic examination of a suspension of bacteria from a colony reveals (a) cellular morphology, (b) cellular arrangement, and (c) motility. These features (See FIG. 12) add additional pieces to the ID puzzle. A gram stain of the sample may also assist the analyst in getting closer to a characterization of the organism. The gram stain is not foolproof however, and can be occasionally misleading because the staining is frequently dependent upon the age of the colony.

Current microbial testing methods call for initial isolation and identification of the organism first and then, if deemed appropriate, i.e. where a pathogen is identified, performing an antimicrobial susceptibility test. In addition, the analyst must decide which microorganism is responsible for the clinical disease in mixed cultures. There are a number of different ways of doing antimicrobial susceptibility testing (AST). Two of them are disk-diffusion and micro dilution.

In recent years, there has been a trend toward the use of commercial broth micro dilution and automated instrument methods instead of the disk-diffusion procedure. However, there may be renewed interest in the disk-diffusion test because of its inherent flexibility in drug selection and low cost. The availability of numerous antimicrobial agents and the diversity in antibiotic formularies in different institutions has made it difficult for manufactures of commercial test systems to provide standard test panels that fit every facility's needs. Thus, the inherent flexibility of drug selection provided by the disk-diffusion test is an undeniable asset of the method. It is also one of the most established and best proven of all AST tests and continues to be updated and refined through frequent National Committee for Clinical Laboratory Standards (NCCLS) publications. Furthermore, clinicians readily understand the qualitative interpretive category results of susceptible, intermediate, and resistant provided by the disk test. It is an ideal method when doing manual diagnostic microbiology A distinct disadvantage of the above prior art is the total time that it takes from obtaining the culture through performing ID and AST. At least three days transpire before results are available. Another disadvantage is the expense to process the specimen using prior art. A further disadvantage of the prior art is the number of steps involved in performing the tests, which increases the likelihood of human error.

A further disadvantage is raised by the limited shelf life of the agar-based microbiology media that is currently used in the art. Specifically, most currently-available agar-based media have a shelf life of from about one to about two months at most. One problem which reduces the shelf life of such media is syneresis, a condition in which the liquid component of the agar media separates from the gel component. This dramatically reduces the utility of the media by segregating the moisture and nutrients needed in all portions of the agar in a liquid phase, rendering the agar uneven in its ability to support sample growth. This restricts the ability of facilities to maintain an inventory of suitable media and complicates the manufacture, distribution, and sale of diagnostic kits utilizing agar-based media currently known and used in the art.

BRIEF SUMMARY OF THE INVENTION

The compounds, methods, and apparatus of the present invention have been developed in response to the present state of the art, and in particular, in response to the problems and needs in the art that have not yet been fully solved by currently available methods, apparatus, and media for use in the concurrent identification and susceptibility testing of microorganisms.

This invention thus relates to methods, apparatus, and media for use in the concurrent identification and antimicrobial susceptibility testing of an unknown microorganism or microorganisms. More specifically, the invention provides specialized media, bacterial identification and antibiotic-susceptibility testing kits constructed using the specialized media, and methods for their use in providing diagnosis of and recommended treatment regimens for infections. The media, kits, and methods of the invention may allow manual determination of the type of infection present in a specimen in periods of about 12 to 24 hours. The invention further provides stabilized culture media useful in a broad variety of applications.

The present method, kit, and media of the invention relate in part to the identification (or "ID") of microorganisms as well as to the concurrent or consecutive determination of antimicrobial susceptibilities (antibiotic susceptibility testing or "AST"). The methods of the invention may allow testing directly from the culture site, without requiring an isolation step. The method and kit offer results quickly in one-third of the time required for standard manual methods.

According to the methods of the invention, the microbes present in a sample may be tested for susceptibility to antimicrobial agents and identified to some level simultaneously. These methods include the steps of applying a portion of the sample containing microbes to a culture plate, applying a fraction of an antimicrobial test disk to the culture plate such that it abuts at least one wall of the plate, incubating the culture plate, and interpreting the results. According to some specific methods of the invention, the step of applying a fraction of an antimicrobial test paper to the culture plate comprises applying a quarter of a standard antimicrobial susceptibility test disk paper to the culture plate. In others, the step comprises applying a half of a standard antimicrobial susceptibility test disk paper to the culture plate. The methods of the invention may be further adapted to utilize similarly-sized segments of test strips and other similar carriers of antimicrobial agents that may be custom-sized, etc. Such test disks are commonly available carrying a wide variety of agents used both in humans and in veterinary applications.

The step of applying a portion of an antimicrobial test paper to the culture plate further specifies that the disk fraction be applied such that it abuts at least one wall of the plate. In methods of the invention in which disk-quarters are utilized, some such methods require that a flat edge of the disk-quarter abut the wall of the plate. In some methods of the invention, the flat edge would be placed such that it abuts a flat wall of the plate. In others, the flat edge would be placed such that it abuts a non-flat, rounded, or arcuate wall of the plate. The method steps may be adapted to allow use of a variety of culture plate configurations, several of which are illustrated in the appended figures. In some configurations, the culture plates comprise a number of substantially square chambers, each providing four corners and substantially flat walls. In others, the culture plate is similar to a standard rounded Petri dish divided into quarters commonly referred to as an X-dish. In such a configuration, each of the four wedge-shaped chambers may be provided with a different culture medium, and each includes a pair of flat wall surfaces, an arcuate surface, and three corners. In each of these chamber configurations, a fraction of an antimicrobial test disk such as a disk-quarter may be applied to a corner of the chamber.

It was discovered that use of a fraction of an antimicrobial susceptibility test disk applied to a wall of a chamber provided antimicrobial susceptibility test results having a predictable relationship to results obtained using full test disks placed centered in a lawn of microbes cultured on a medium (Kirby-Bauer or Bauer-Kirby method). In the methods of the invention, the antimicrobial paper is placed at the edge or in the corner of chamber to obtain equivalence. More specifically, according to the methods of the invention, the radius of the zone of inhibition created by the placement of a disk-fraction such as a disk quarter is measured. This radius is then multiplied by two, resulting in a measurement that approximates the diameter measurements taken in traditional Kirby-Bauer susceptibility tests. This allows the radius measurement obtained to be converted to a value usable in standardized antimicrobial susceptibility tables for evaluation of microbial susceptibility or resistance to a particular agent such as NCCLS interpretive standards charts known to one of ordinary skill in the art. Thus, according to the methods of the invention, the step of interpreting the results may comprise the steps of measuring the radius of the zone of growth inhibition present about the fraction of the antimicrobial test paper, multiplying it by an adjustment factor, which is most commonly 2, and comparing it with a standard table of antimicrobial susceptibilities.

The invention further provides kits for performing the antimicrobial susceptibility testing methods of the invention. Such kits may include a culture plate, the plate including a first chamber comprising a growth medium supporting the growth of a gram-positive organism, a second chamber comprising a growth medium supporting the growth of a gram-negative organism, and a third and possibly fourth chamber comprising a growth medium supporting the growth of a broad variety of organisms; and at least one fraction of an antimicrobial test paper configured to be applied to the culture plate abutting at least one wall of the plate.

The kits and methods of the invention may use a wide variety of suitable culture media formulations. The agar-based media formulated using carrageenan taught in the parent application may be used to extend the useful shelf life of the media, as well as the useful shelf life of kits produced using the media of the invention. Some kits, however, are produced without the carrageenan-fortified agar media. The carrageenan-infused culture media of the invention result in a reduction of syneresis, thus providing potential improved performance of the media. The kits of the invention produced with the carrageenan-stabilized culture media may have a shelf life of from about 3 to about 12 months. In some embodiments, the kits may have a shelf life of at least about 5 months from date of manufacture when stored at 4° C. Additionally the kits may be packaged in a sealed pouch possessing low oxygen permeability, such as nylon/EVOH/poly, with or without an oxygen absorbing packet or strip inserted. This process may further enhance the shelf life of the products.

The kits of the invention may employ a disposable multi-chambered plate (kit plate) with at least one, but generally at least two types of culture media including, but not limited to: enriched, differential, selective, and differential-selective media in addition to AST medium. Broth medium may be provided with the kit for increasing the volume of microorganisms present in a sample such as a blood specimen, in preparation for eventual inoculation onto the kit plate when necessary or desirable. In addition, a variety of AST disk-quarters may be included in the kit, as may other biochemical reagents for colony spot testing, known to one of ordinary skill in the art that would be useful for additional identification.

The invention thus comprises specialized media, methods, and kits for in-house or in-the-field characterization and/or antimicrobial susceptibility testing of unknown microorganisms. The size and complexity of the kit may be readily adapted to provide a variety of levels of microbial identification. The kit may be provided such that it comes complete with all components and equipment needed to perform the testing except for an incubator. A portable incubator can be operated from any direct current source such as an automobile battery. As a result, the kit is well suited in areas where microbiology laboratories are scarce or unavailable. In addition, the kit serves to obtain rapid AST information. Microorganisms such as Anthrax (*Bacillus anthracis*) can be identified concurrently with drug susceptibility testing within 24 hours.

As discussed above, many antimicrobial agents are no longer effective against certain strains of bacteria. AST is useful and important for the common microorganism species that are not predictably susceptible to drugs of choice because of acquired resistance mechanisms (e.g., members of the Enterobacteriaceae, the *Pseudomonas* species, *Staphylococcus* species, *Enterococcus* species, *Streptococcus pneumoniae, Haemophilus influenzae*, and *Neisseria gonorrhoeae*). A recent editorial in the British Journal of Medicine states: "Research is also a cornerstone in the fight against bacterial resistance. We have to improve our understanding of microorganism flora, the evolution of resistance, and the mechanisms of transmissibility of resistant bacteria. New diagnostic technologies to enable rapid ID of viral and bacterial infections are also necessary: for too long it has been easier for clinicians to prescribe an antibiotic than to make a specific diagnosis". P. Huovinen & O. Cars, BMJ 317:613–614 (1998).

The media, methods, and kits of the invention may provide a method and kit where a specimen from the site of infection or a microorganism-containing sample can be immediately applied directly to the plate media. This renders the use of transport media unnecessary. Therefore, the specimen is not subjected to time delays; possible adverse environmental conditions or excessive drying that would compromise its integrity. Fluid specimens can also be immediately processed. In addition, a more rapid result is realized with this system due to immediate inoculation.

The invention may further provide a method and kit comprising a multi-chambered, easily visualized culture kit plate comprising a battery of different media with diagnostic functionality. The multi-kit plate media performs the ID and AST of gram-negative and gram-positive organisms. In some embodiments, one chamber may be devoted to fungal determination. Errors or misjudgments in the prior art of media selection may be avoided with the present system. An appropriate selection of medium is already-incorporated in the design of the multi-chambered kit plate. This may assure that the user of the kit will not be caught short in making a definitive diagnosis due to incorrect media selection.

The invention may additionally provide alternate kits using multi-chambered culture plates with a more limited range of media configured to provide presumptive identification to a broader level while also allowing antimicrobial susceptibility testing. The media provided in such kits may be selected to provide ideal growth conditions for organisms suspected to be present in an individual or population. Similarly, the type and number of test disk-quarters used and/or provided with the kit may be adjusted to test for specific organisms or groups of organisms. One embodiment comprises a three or four-chambered dish. The specimen is added directly (or diluted and added) to several chambers, where susceptibility testing may be done using a calibrated loop which allows for later determination of colony forming units per unit volume. Antimicrobial susceptibility testing is performed using multiple antimicrobial agents placed in corners and along edges of selected chambers. The remaining chambers are used for performing classic colony isolation and presumptive ID using enriched, differential or selective media. A more definitive ID can be carried forward if desired, from the isolates.

The invention provides a method and kit for concurrent ID and AST. The novel Kirby-Bauer disk-diffusion method used with this kit allows for flexibility in terms of choice of antimicrobial agents. The method of placing the antimicrobial agents into the AST test chambers is quick, using a novel method. The resultant zone size is measured as radius whereas in a prior art standard method, zone size is measured as diameter which is exactly twice the value of the miniature assay. This allows the use of the NCCLS interpretative standards charts divided by 2. Another advantage is manifest when there is more than one organism on the kit plate. When more than one zone is evident, morphology of the more resistant organism (inner zone) can be observed by taking a sample of inner zone bacteria and observing microscopically. It has been observed that routine cultures that grow three or more organism types should be discounted. Specimens obtained from non-sterile sites most commonly represent colonization or contamination. The most ideal situations for the use of the kit are those in which the specimens come from body sites normally devoid of flora such as: blood; closed cavity body fluids such as CSF, synovial, pleural, pericardial, amniotic, etc; urine; lower respiratory tract; eye; wounds; and bone and tissue. See FIG. 15.

The invention may additionally provide a kit and method for ID, while also featuring a direct AST that can yield results in as little as one-third the time of the prior art methods. The patient can start on the correct antimicrobial agent by the next day and avoid having to take an incorrect empirical antimicrobial agent for a 3-day period, as would be the case in the prior art. Where the infection is life threatening, it is a powerful approach to the problem.

The invention further provides a kit and method for ID and AST where the kit plate component has a shelf life of from about 3 months to about 12 months, or in some specific embodiments at least 5 months when stored at 4° C. As noted above, the invention provides media incorporating carrageenan which exhibit enhanced shelf-stability, and thus an expanded shelf life. In some embodiments, the media of the invention incorporate up to about 0.5% iota carrageenan. In other embodiments, the agar-based media of the invention include up to about 0.1% to about 1.0% iota carrageenan. In still other embodiments of the invention, the media of the invention include up to about 0.2% iota carrageenan.

In one embodiment, the invention performs a direct antimicrobial susceptibility test on the major bacterial species present in a clinical specimen with results in 12 to 18 hours. Additionally, the embodiment provides a snapshot of the actual bacterial population of the sampled infection site. When more than one type of organism is present, the embodiment eluded to, can differentiate between them. Results reveal the following: (1) the antimicrobial agent(s) that are effective (in vitro) against the cultured pathogens(s); (2) actual colony forming units per unit volume; (3) when more than one organism is present, a picture of the actual relative quantities of the different bacterial species present in the specimen; (4) identification of gram (+) and gram (−) levels; and (5) isolated colonies for additional testing if desired.

These and other features and advantages of the present invention will become more fully apparent from the following figures, description, and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. The patent or application file contains at least one drawing executed in color. Copies of this patent or patent application publication with color drawing(s) will be provided by the Office upon request and payment of the necessary fee.

Understanding that these drawings depict only typical embodiments of the invention and are not therefore to be considered to be limiting of its scope, the invention will be described and explained with additional specificity and detail through the use of the accompanying drawings in which:

FIG. 2E is a photograph of a kit plate antimicrobial susceptibility test, as practiced in the invention, for comparison to FIGS. 2C and 2D.

FIG. 2F is a table comparing the results of the tests illustrated in FIGS. 2C, 2D and 2E, where the same pathogen and antimicrobial agents were used;

FIG. 3A compares the results of antimicrobial susceptibility testing performed with full disks and disk-fractions in the same plate;

FIG. 3B compares the results of antimicrobial susceptibility testing performed with disk-halves and disk-quarters in the same plate;

FIG. 3C is a table comparing the results obtained from the tests of FIGS. 3A and 3B;

FIG. 9 is a table of the characteristics of various colonies of bacteria potentially found on culture plates of the invention;

FIG. 10 is a flow chart which may be used in the methods of the invention to identify and determine significance as well as quantitate bacterial colonies present on the kit plate following incubation;

FIG. 11 illustrates two direct biochemical spot tests and lists five others that may be used in the further identification of bacterial colonies present, at the end of the incubation period.

FIG. 12 is a table of the cellular morphology of individual microbes potentially found on culture plates of the invention;

FIG. 13 shows a table of interpretive standards of a set of nine antimicrobial agents used with several embodiments of the kit of the invention.

FIGS. 14A and 14B show a more extensive interpretive standards table listing prior art zone diameters adjacent to kit utilized zone radii.

FIG. 15 provides a table of biological specimens and microbes commonly isolated from each specimen type.

DETAILED DESCRIPTION OF THE INVENTION

The present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in FIGS. 1 through 18, is not intended to limit the scope of the invention, as claimed, but is merely representative of presently preferred embodiments of the invention.

Figure 1A:
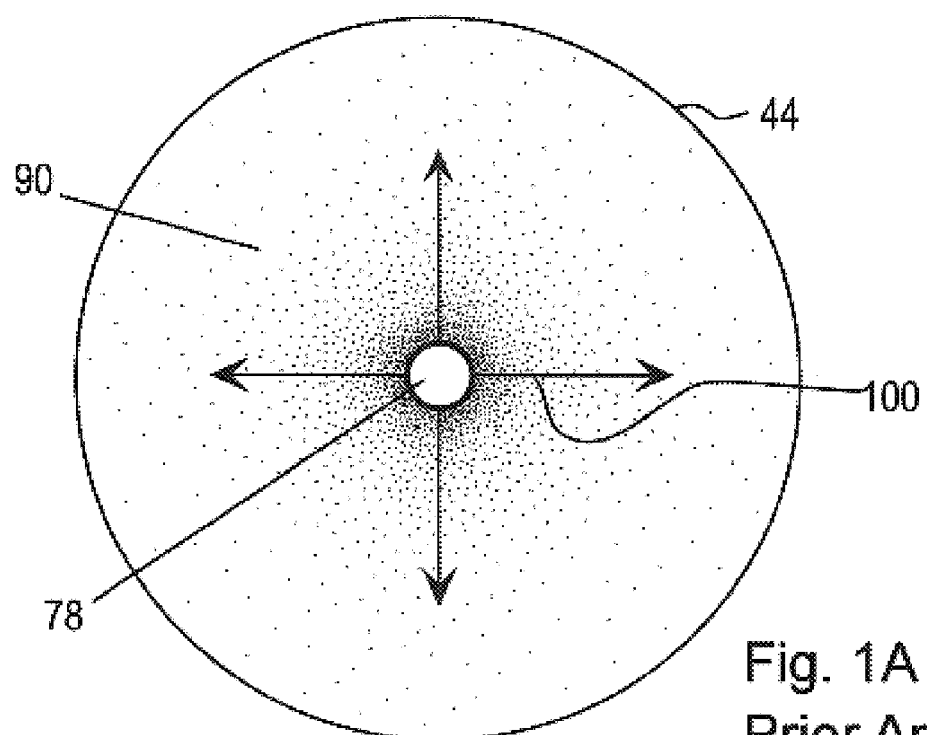
FIG. 1A illustrates the principle of the standard Kirby-Bauer disk-diffusion test known in the art.
Figure 1B:
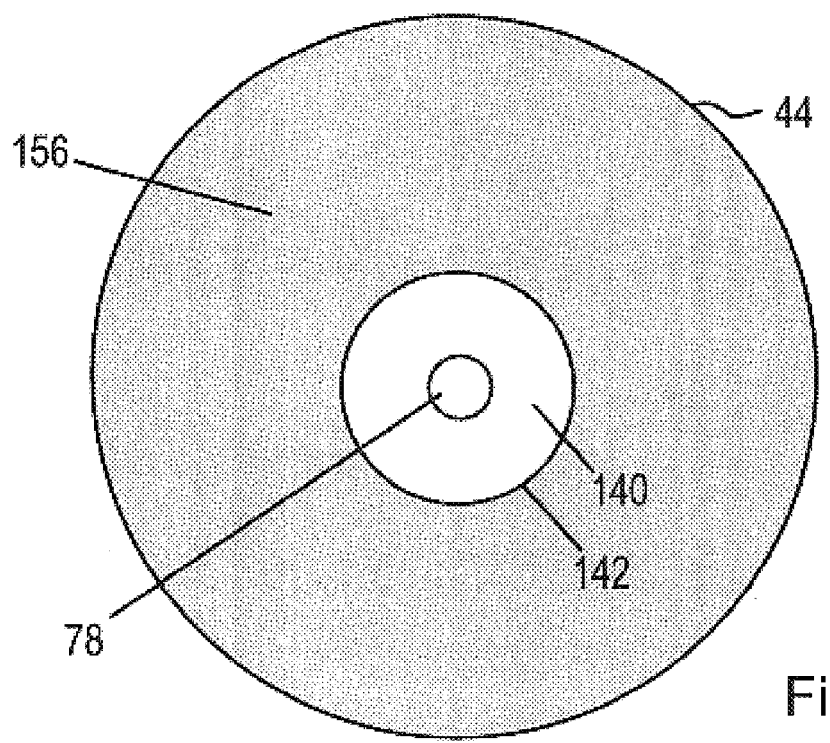
FIG. 1B further illustrates principles involved in standard Kirby-Bauer-testing.

In traditional Kirby-Bauer antimicrobial susceptibility testing, as illustrated in FIG. 1A, a Petri dish of sufficient dimension is provided. The dish contains a standardized medium such as Mueller Hinton. The medium is then inoculated with a sample of bacteria and becomes known as sample-inoculated medium 90. A disk 78, containing a selected antimicrobial agent is placed on the sample-inoculated medium 90 in a central region, such that the disk 78 is distanced from walls or other structures on the plate 44. The antimicrobial agent diffuses outwardly from the disk 78 into the sample-inoculated medium 90; forming a concentration gradient 100 with decreasing concentration outwardly from the position of the disk 78. Referring next to FIG. 1B, the plate has been incubated for a period of time allowing for the microbes to multiply to a visible growth 156. If their growth is prevented or inhibited by the agent present in the disk 78, a zone of inhibition 140 is formed about the disk 78. A margin 142, which is the interface between growing and inhibited bacteria, and is the point at which the concentration of antimicrobial agent no longer inhibits bacterial growth 156.

Figure 2A:
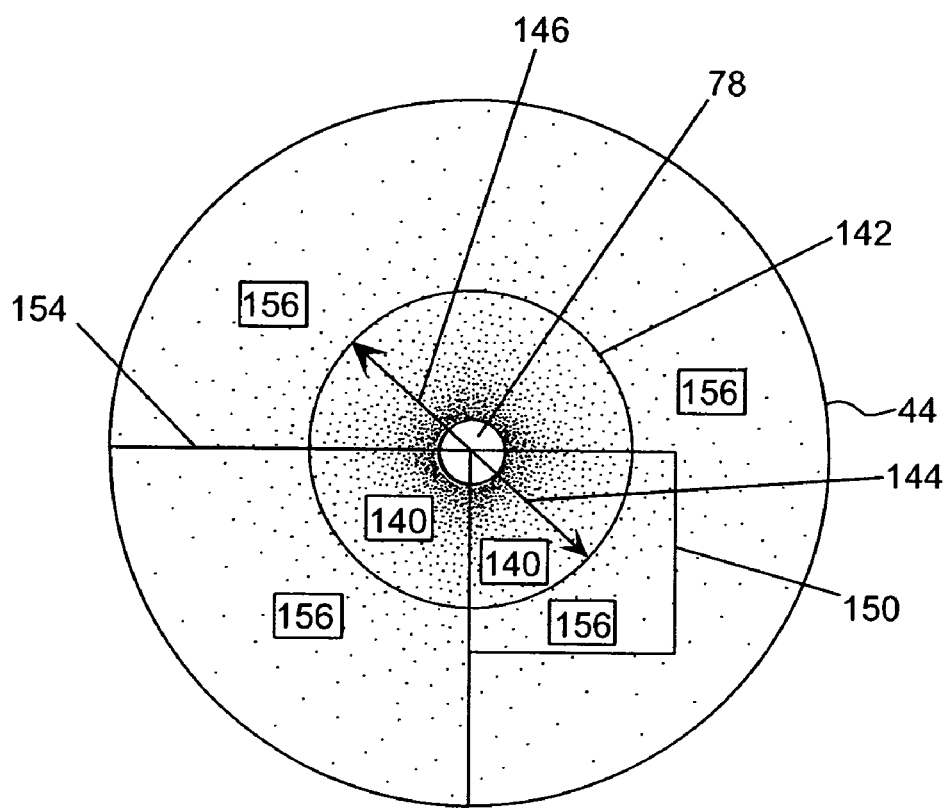
FIG. 2A illustrates the principle behind the system of the invention relative to standard Kirby-Bauer methods.

As in FIG. 1A, in FIG. 2A, the concentration gradient 100 of antimicrobial agent is portrayed by the field of dots arrayed densely when proximate to the disk 78 and more diffusely when distal to the disk 78. The traditional Kirby-Bauer test shown in FIG. 2A illustrates the manner by which such a test is used to evaluate susceptibility of organisms in culture to a given antimicrobial agent. In such tests, as explained briefly above, an antimicrobial test disk 78 is placed on the plate 44. The margin 142 is formed as bacteria grow 156 only up to a point where they are inhibited by the antimicrobial agent diffusing out of disk 78 forming a concentration gradient. Susceptibility of the microbes present in the culture is determined by measuring the diameter 146 of the zone of inhibition 140 defined by the margin 142. This measurement is taken and weighed against values presented in standardized tables.

Figure 16:
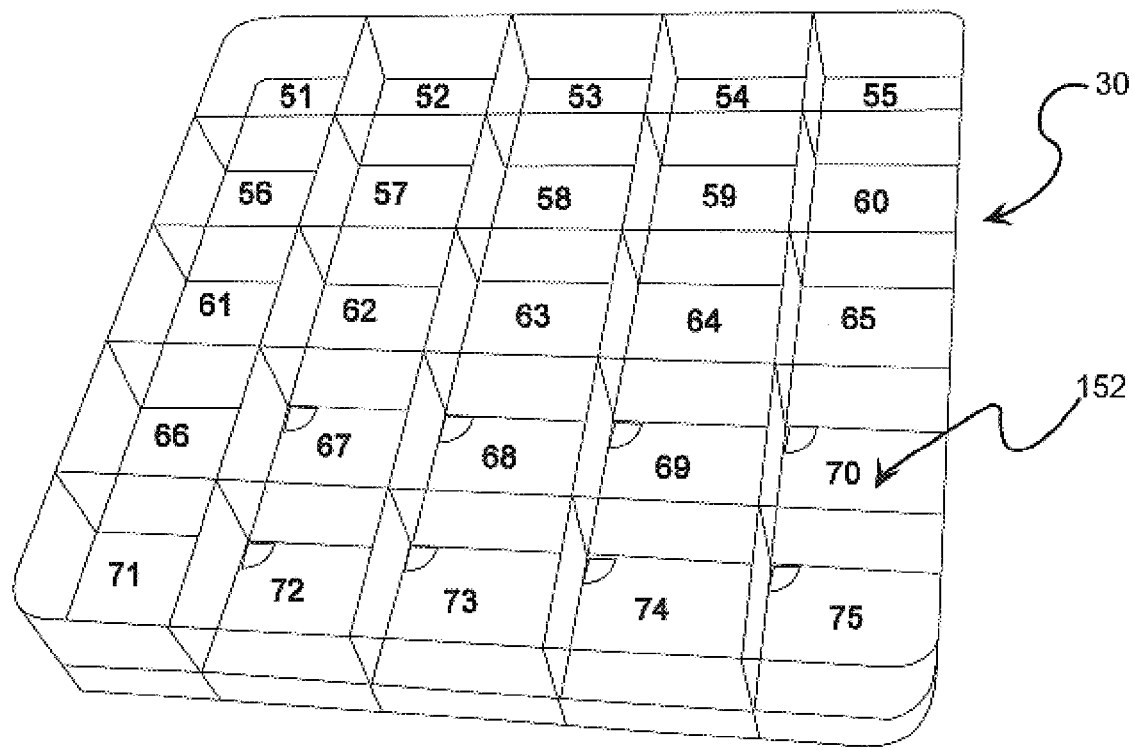
FIG. 16 shows a perspective view of a multi-chambered kit plate of the invention with substantially square test chambers, eight of the test chambers illustrating antimicrobial disk-quarters placed in the corners.

FIG. 2A further comprises a hypothetical square 150, of like dimensions to a chamber 152 of FIG. 16, capturing one-quarter of the test disk 78 and a portion of the plate 44. This segment 150 equates to the chamber 152 of FIG. 16 shown isolated for further discussion in FIG. 2B. Referring to either FIG. 2A or 2B, according to the methods of the invention, the placement of a disk-fraction 76 such as a disk-quarter to abut walls of a plate-chamber 152 illustrates a principle utilized in the methods and kits of the invention. Namely, it has been discovered that placement of a fraction such as a quarter 76 of a standard AST disk 78 in a chamber 152 in corner or even at a position abutting at least one wall produces a zone of inhibition 140 having a radius 144 substantially similar to the radius 144 of the zone of inhibition 140 observed in a standard Kirby-Bauer test. The same results hold true for a quarter pie 154 of plate 44 for placement of disk fraction at center corner. In fact, the equivalence holds true for any position along and abutting the inner wall of the quarter-pie chamber. The same holds true for any shaped chamber with the fraction abutting anywhere against inside wall of the chamber. Thus, according to the methods of the invention, the radius 144 is measured, multiplied by two, and the resulting value is compared with tables such as FIGS. 14A and 14B used with standard Kirby-Bauer tests to interpret the results.

Figure 2B:
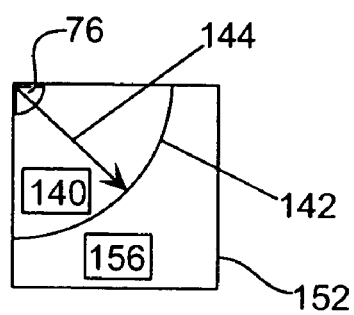
FIG. 2B is a detailed view of the portion of the culture plate illustrated in FIG. 2A and FIG. 16.
Figure 2C:
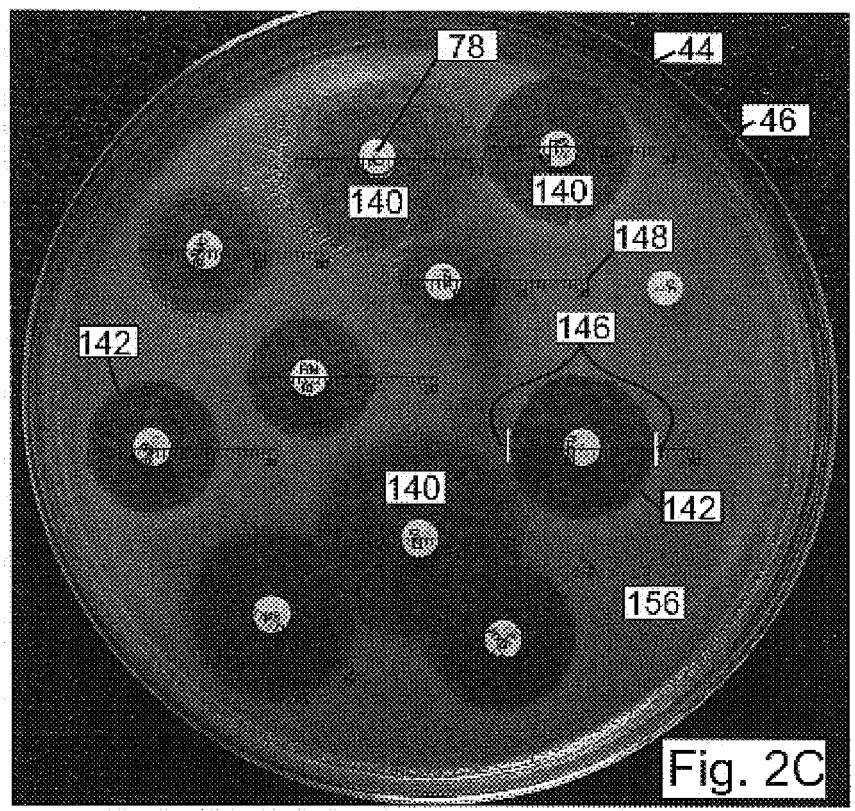
FIG. 2C is a photograph of a Kirby-Bauer antimicrobial susceptibility test performed as practiced in the art.

FIG. 2C is a photograph of a test plate 44 on which a standard Kirby-Bauer test is being performed using eleven different AST disks 78 with sample-inoculated medium 90. The plate 44 was inoculated with *E. coli* and incubated for 18 hours with the disks 78 in place. The bacterial growth 156 is evident up to the margins 142 and zones of inhibition 140 of the respective AST disks. Each of the disks 78 producing a zone of inhibition 140 was then overlaid with a scale 148 measured in millimeters for measuring the diameter 146 of the zone of inhibition 140 produced by the disk 78. These diameter measurements 146 are found in FIG. 2F and labeled FIG. 2C, discussed in greater detail below, in which each disk 78 has an abbreviated label corresponding to the name of an antimicrobial product.

Figure 2D:
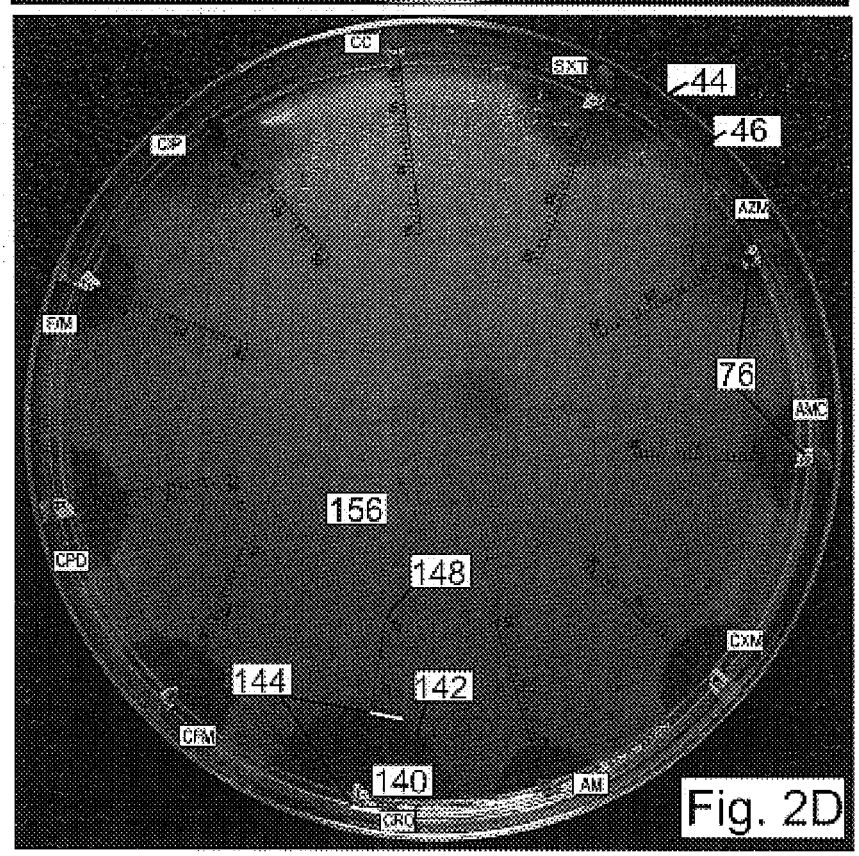
FIG. 2D is a photograph of the antimicrobial susceptibility test performed as taught in the present application.

FIG. 2D is an AST test conducted according to the methods of the present invention in which, using a substantially identical culture plate with growth medium and an identical *E. coli* inoculate, ¼ fractions 76 of the same AST disks 78 used in the traditional Kirby-Bauer methods illustrated in FIG. 2C are placed abutting the inner wall 46 of the culture plate 44 and the plate 44 was incubated for 18 hours. Thus placed, the disk fractions 76 produce substantially semicircular zones of inhibition 140. Each disk-quarter 76 is overlaid with a scale 148 measuring (in millimeters) the radius 144 of the zone of inhibition 140 associated with each disk-quarter 76. These radius measurements 144 are found in FIG. 2F and labeled FIG. 2D. As with FIG. 2C AST disks 78, each disk quarter 76 has an abbreviated label corresponding to the name of an antimicrobial agent.

Referring next to FIG. 2E, a kit plate 310 according to the invention is shown. Kit plate 310 is a standard X-dish divided by walls 212 such that it provides four wedge-shaped chambers 220A, 220B, 220C, and 220D. The chambers may each be filled with a culture medium. In the embodiment of the kit plate 310 illustrated in FIG. 2E, each chamber 220A, 220B, 220C, and 220D is filled with a different medium. In FIG. 2E, chamber 220A includes Columbia CNA with Blood medium 222A, chamber 220B includes MacConkie agar medium 222B, chamber 220C includes Chocolatized blood agar medium 322C, and chamber 220D includes Mueller Hinton agar with blood medium 222D, respectively. Although the agar types may vary and be arrayed in many ways, in FIG. 2E, chambers 220A and 220B are filled with agar types (222A, 222B) selected to distinguish between gram-positive and gram-negative bacteria. Chambers 220C and 220D, however, incorporate agar media capable of culture of a wider variety of microbes, and may thus be used for the AST steps of the invention. FIG. 2E illustrates one example of positioning test disk quarters 76 in corners and abutting inner walls 46 on the culture plate 310 for AST: Thus placed, the disk fractions 76 produce substantially semicircular zones of inhibition 140. Each disk-quarter 76 is overlaid with a scale 148 measuring (in millimeters) the radius 144 of the zone of inhibition 140 associated with each disk-quarter 76. These radius measurements 144 are found in FIG. 2F and labeled FIG. 2E. As with FIG. 2D, each disk quarter 76 has an abbreviated label corresponding to the name of an antimicrobial agent.

In FIG. 2F, the diameter measurements obtained from the traditional Kirby-Bauer test are compared with the radius measurements obtained from the AST method of the invention as shown in 2D and 2E. In the table of FIG. 2F, abbreviations the used to mark each of the disks 78 and disk-quarters 76 are used to identify the corresponding disk 78 or disk-quarter 76. The abbreviations are used to denote the antimicrobial agent present in the disk 78 or disk-quarter 76. In FIG. 2F, "AM" corresponds to ampicillin; "AMC" corresponds to amoxicillin/clavulanate; "AZM" corresponds to azithromycin; "CFM" corresponds to cefixime; "CPD" corresponds to cefpodoxime; "CXM" corresponds to cefuroxime; "CC" corresponds to clindamycin; "CIP" corresponds to ciprofloxicin; "CRO" corresponds to ceftriaxone; "F/M" corresponds to nitrofurantoin; and "SXT" corresponds to trimethoprim/sulfamethoxazole. In each case, multiplying by 2 the radius 144 of the zones of inhibition 140 produced by the disk-quarters 76 provides a number either identical to or substantially identical to the diameter 146 measurement obtained in the standard Kirby-Bauer test.

A comparison of FIGS. 2C, 2D, and 2E also illustrates at least one other benefit of the novel methods of the invention: namely, that the methods of the invention provide results that are as informative as those obtained in a traditional Kirby-Bauer test, but may be conducted in a much smaller area, thus opening the potential for a compact kit that allows the performance of multiple AST tests in a small area.

Referring next to FIG. 3A, an additional kit 410 according to the invention is shown. In kit 410, chambers 220A, 220B, include Columbia CNA blood agar medium 222A, and MacConkie agar medium 222B, respectively, while chambers 220C, 220D include Mueller-Hinton agar medium 222C. Each chamber 220A, 220B, 220C, 220D was inoculated with *E. coli* as taught herein. Following this, disk-quarters 476 and whole disks 478 all containing the same antimicrobial agent were placed in chambers 220C, 220D as illustrated, and the kit 410 was subsequently incubated for 18 hours. FIG. 3B provides another kit 410, in which chambers 220A, 220B, include Columbia CNA agar with blood medium 222A, and MacConkie agar medium 222B, as above, while chambers 220C, 220D include Mueller-Hinton agar medium 222C. Each chamber 220A, 220B, 220C, 220D was inoculated with *E. coli* as taught herein as in FIG. 3A. In kit 410 of FIG. 3B disk-quarters 476 and half disks 480 all containing the same antimicrobial agent as used in 3A were placed in chambers 220C, 220D as illustrated, and the kit 410 was subsequently incubated for 18 hours. This provided a comparison of the results of the tests of the invention when disk-quarters 476 were used with the results of disk-halves 480. The results of these tests are illustrated in FIG. 3C. As seen in FIG. 3C, the radii 144 measured for both the disk quarters 476 and disk-halves 480 are nearly identical, and are also both substantially ½ of the value of the diameter 146 measured when the full disk 478 was used.

Thus, the invention provides methods of conducting antimicrobial susceptibility testing that are equivalent to the standard Kirby Bauer antimicrobial susceptibility test. Methods of the invention are suitable for being conducted in a more rapid manner than currently-known techniques in less space, and using smaller amounts of input materials. This speeds the availability of test results and lowers the cost of tests provided, all while maintaining accuracy and legitimacy.

Figure 4:
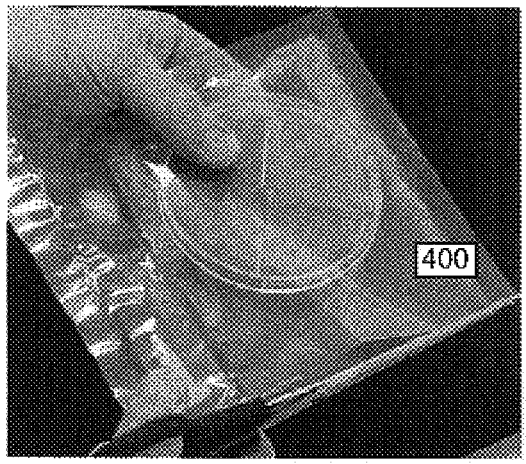
FIG. 4 shows a photograph of packaging the kit plate using a nylon/EVOH/poly pouch (shown), with or without an oxygen absorbing packet or strip (not shown).

FIG. 4 shows a photograph of one method of packaging 400 kit plate using a nylon/EVOH/poly pouch, with or without an oxygen absorbing packet or strip (not shown). Along with the addition of iota carrageenan to the kit media, this type of packaging may further increase the shelf life of the kit. In addition, any storage package with or without an oxygen absorbing feature, that lowers oxygen contact on kit plate may be effective.

Figure 5A:
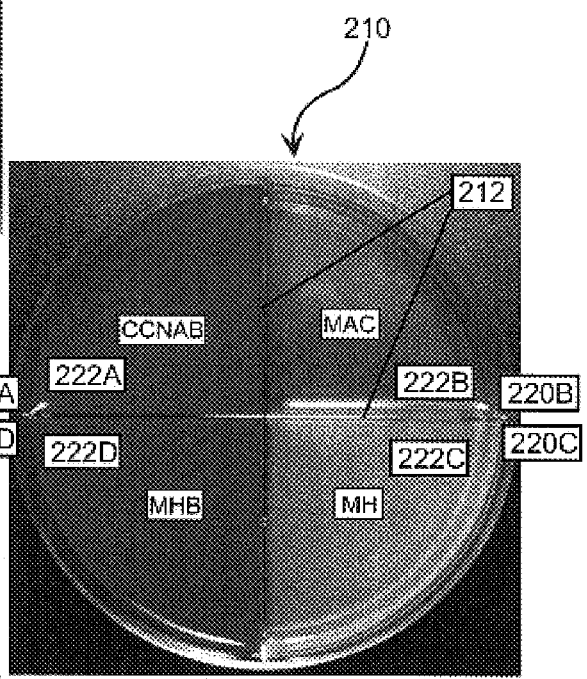
FIG. 5A shows an embodiment of kit plate comprising carrageenan-fortified agars prepared according to the invention and used in methods of present invention.

Referring next to FIG. 5A, another embodiment of the test kit plates 210 according to the invention is illustrated. Kit plate 210 is a standard X-dish divided by walls 212 such that it provides four wedge-shaped chambers 220A, 220B, 220C, and 220D. The chambers may each be filled with a culture medium 222. In the embodiment of the kit plate 210 illustrated in FIG. 5A, each chamber 220A, 220B, 220C, and 220D is filled with a different medium 222. In FIG. 3, chamber 220A includes Columbia CNA with Blood medium 222A, chamber 220B includes MacConkie agar medium 222B, chamber 220C includes Mueller Hinton agar medium 222C, and chamber 220D includes Mueller Hinton agar with blood medium 222D, respectively. Although the agar types may be arrayed in many ways, in FIG. 5A, chambers 220A and 220B are filled with agar types (222A, 222B) selected to distinguish between gram-positive and gram-negative bacteria. Chambers 220C and 220D, however, incorporate agar media capable of culture of a wider variety of microbes, and may thus be used for the AST steps of the invention.

Figure 5B:
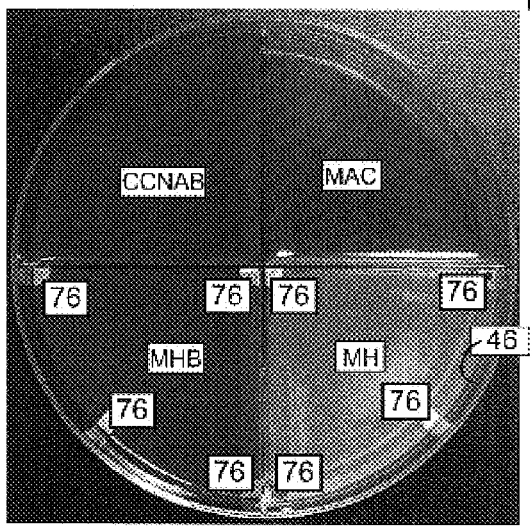
FIG. 5B shows the test plate of FIG. 5A to illustrate one scheme for laying out the antimicrobial disk-fractions taught in the present invention.

FIG. 5B illustrates one example of positioning test disk quarters 76 on the culture plate 210, namely, one disk quarter 76 in each of the three corners of chambers 220C and 220D, and one disk quarter 76 positioned along the inner wall 46 of chambers 220C and 220D.

Figure 5C:
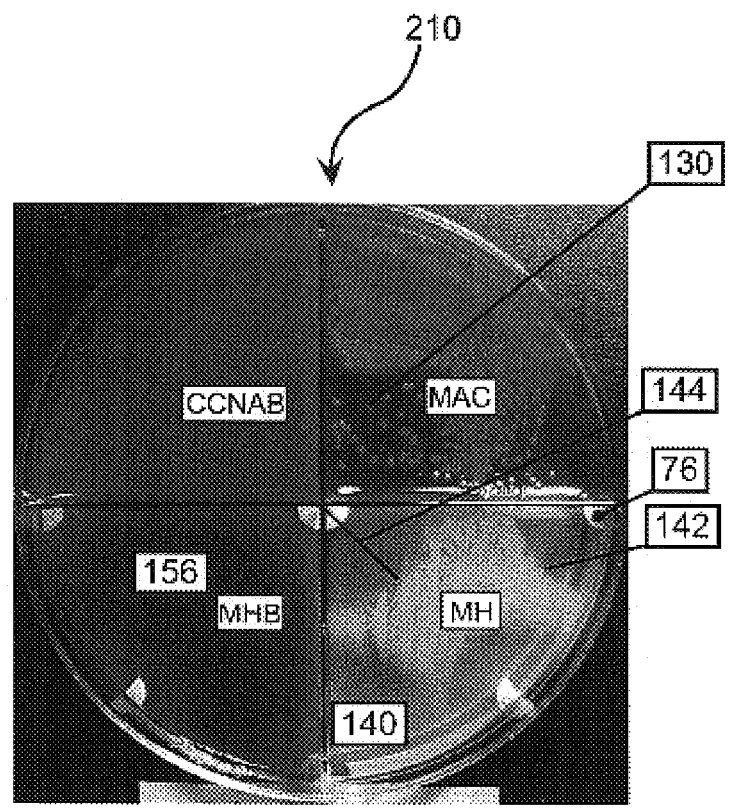
FIG. 5C is a photograph of a kit plate according to the invention showing zones of inhibition of the antimicrobial susceptibility test and pathogen colony isolation on MAC medium, following incubation with a pathogen.

FIG. 5C illustrates the effect of incubation of kit plate of FIG. 5B with a sample of *E. coli* bacteria. The results show inhibition by CCNAB, growth and isolation of colonies 130 on MAC (expanded in method description below), and bacterial growth 156, zones of inhibition 140 for the various AST disk quarters 76, margins 142 and measurement of radii 144.

Figure 6:
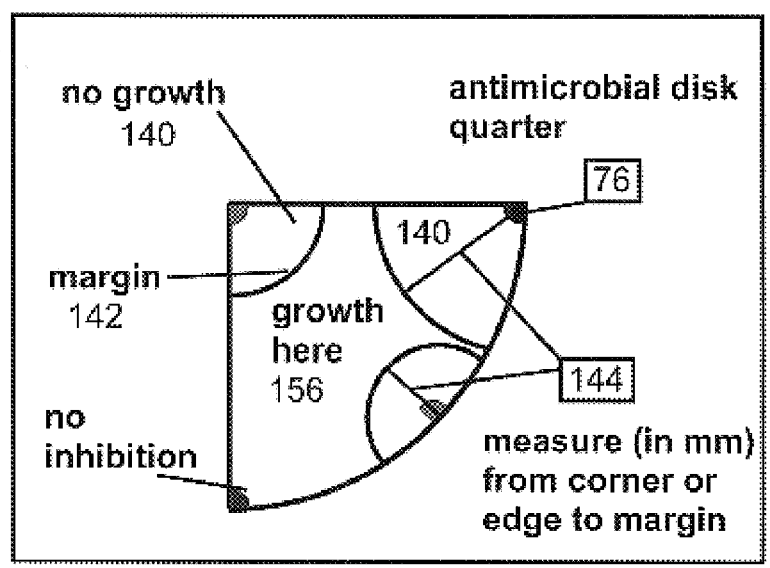
FIG. 6 is a diagram of an antimicrobial test chamber of the kit plate following incubation, illustrating various features of a result.

FIG. 6 provides a diagram illustrating a potential layout for the placement of disk-fractions 76 useful for AST testing in a quarter of a kit plate 210. The diagram of FIG. 6 also illustrates bacterial growth 156, zones of inhibition 140, margins 142, and measurement of radii 144 (the measurements needed to interpret the results of the test).

Microbial Identification and Antimicrobial Susceptibility Testing Kit and Method This embodiment of the invention is a testing kit having reduced dimensions and a reduced number of agar chambers compared to the 25 chamber plate described later. In this embodiment of the testing kit within the scope of the invention, the kit plate may be a four-chambered plate, the kit plate is generally a sterilized ethylene oxide-sterilized polypropylene multi-chambered kit plate. One such suitable plate is a Petri dish divided into substantially equal quarters. According to this embodiment of the invention, the four-chambered plate is prepared by partially-filling one chamber with Mueller Hinton blood agar, another chamber with Mueller Hinton agar, another chamber with MacConkey agar, and the final chamber with Columbia CNA blood agar. According to the invention, the agar preparations used in the testing kit may be the carrageenan-stabilized agar-based gels of the invention to provide a longer shelf life and a more syneresis-resistant agar.

The particular carrageenan-stabilized agars used in the kit may be chosen to allow identification of a wide variety of organisms. Mueller Hinton Blood agar may be used to culture the majority of aerobic gram-positive and grain-negative bacteria. In addition, it is a preferred media for AST for more fastidious bacteria such as *streptococcus*. Mueller Hinton grows a similar range of microorganisms, but also it is a preferred media for AST. MacConkey agar may commonly be provided in a formulation including lactose. In such formulations, MacConkey agar will support the growth of 100% of Enterobacteriaceae genera and 80% of other gram-negative genera, while inhibiting the growth of gram-positive organisms. When lactose is provided in the medium, MacConkey agar may allow the determination of whether the bacteria ferment lactose based on the red or pink color of the colony. Columbia CNA blood agar allows the growth of gram-positive organisms while inhibiting the growth of gram-negative organisms. Columbia CNA blood agar also allows discernment of various types of hemolysis conducted by the bacteria: alpha hemolysis results in greenish discoloration of the culture medium, beta hemolysis is exhibited by the lysis of red blood cells in the media, resulting in a clear zone surrounding the colony, gamma shows no hemolysis, and alpha-prime hemolysis is shown by a small zone of complete hemolysis surrounded by a second zone of partial hemolysis. One example of a kit plate comprising carrageenan-fortified Mueller Hinton blood agar (MHB), Mueller Hinton agar, MacConkey agar (MAC), and Columbia CNA blood agar (CCNAB) is shown in FIG. 7.

The testing kit plate thus produced may be used to identify bacteria to the gram (+)/gram (−) level, tests for anaerobes, and allows susceptibility testing against at least about 8 antimicrobial agents. This kit is typically used with 12–24 hour incubation periods. As shown in FIG. 7, this particular embodiment of the testing kit plate may comprise a portion of a kit including the kit plate 210 with lid 211, a tube containing sterile water 82 for dilution, a 10 microliter calibrated loop 84, a sterile culture stick 80, eight to fourteen antimicrobial disk-quarters 76, a disk-quarter applicator 88, and spreading loops 86. Alternatively, the kit plate may be sold alone, with subsets of the above-listed equipment, or with additional equipment. As noted above, the kit plate is used in assays to identify microbes and determine their susceptibility to antimicrobial agents.

Figure 7:
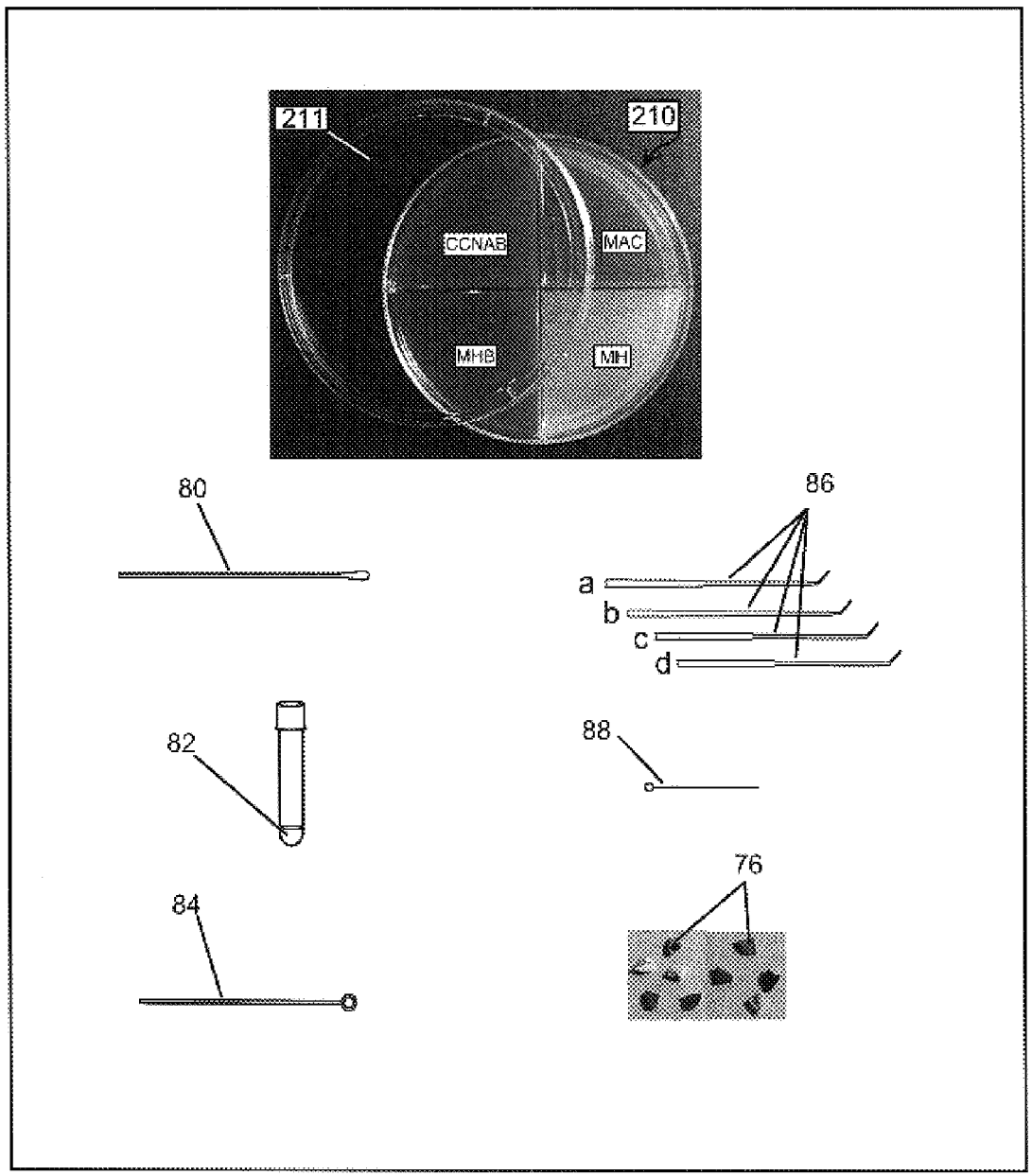
FIG. 7 illustrates an embodiment of a kit of the invention containing components necessary to perform identification and antimicrobial susceptibility testing.
Figure 8A:
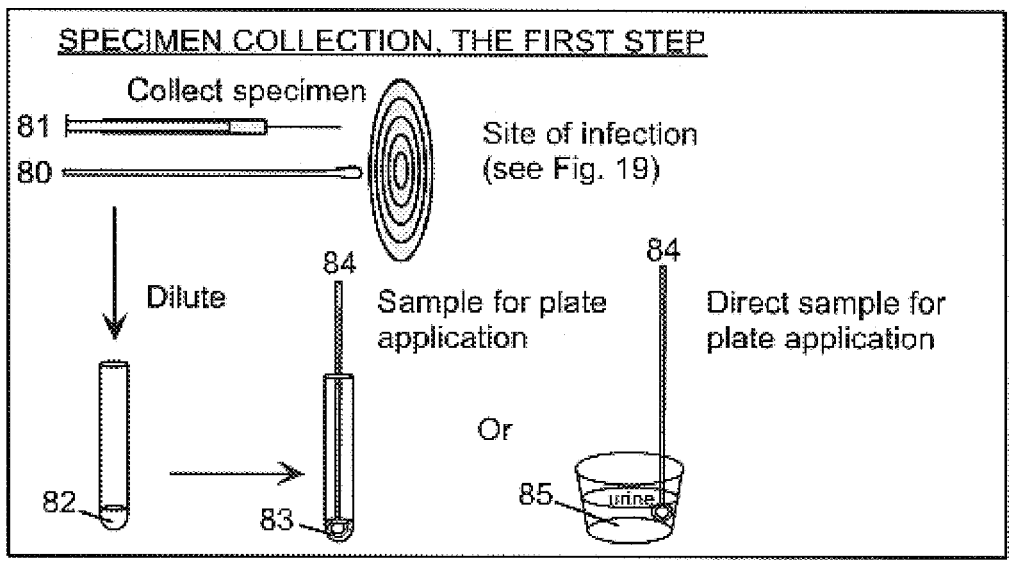
FIG. 8A illustrates several methods of specimen collection and sampling for kit plate application.
Figure 8B:
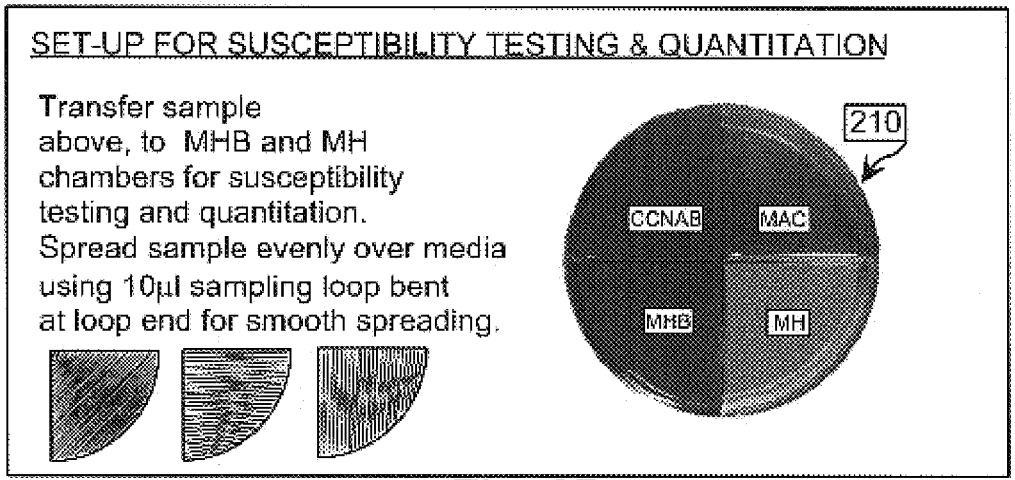
FIG. 8B illustrates a method of applying a microbial sample to a chamber of a test kit of the invention for AST.
Figure 8C:
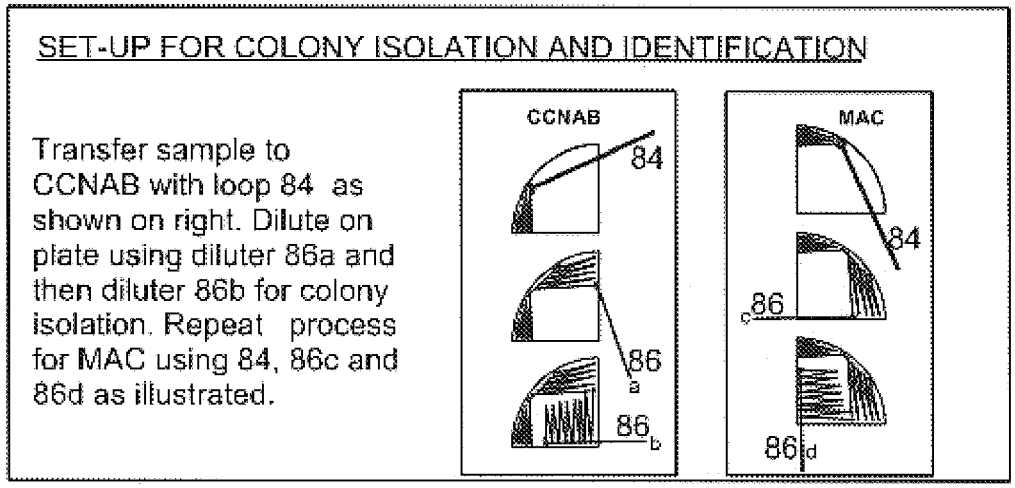
FIG. 8C illustrates a method of applying and diluting a microbial samples to two chambers of a test kit of the invention for ID.

According to one method of using the kit as show in FIG. 7, a sample of interest, taken from the site of infection FIG. 8A with sterile swab 80 or syringe and needle 81, and diluted in sterile water 82 or, if urine for instance 85, is added directly to the plate. See FIGS. 9A, 9B and 9C. About ten to fifty microliters of sample is applied to the Mueller Hinton blood agar chamber and Mueller Hinton agar using the ten microliter loop as shown in FIG. 8B. The loop end is bent for smooth spreading. Proper application of the sample to the chambers where AST is done generally involves spreading the sample uniformly over the two chambers as shown in FIG. 8B. The method of applying sample to the MacConkey and Columbia CNA chambers is illustrated in FIG. 8C. This method allows for the growth of isolated bacterial colonies. See FIG. 5C colony 130. Starting with CCNAB chamber (FIG. 9C), transfer and spread 10 microliters or other volume of sample with loop D in corner of chamber. Return loop to tube or cup. Dilute sample on agar surface using diluters a and b as shown. Make sure the loop end of diluter is bent at an angle, so that the loop rides flat on the surface. The process is repeated for MAC chamber illustrated in FIG. 9C using loop D again to transfer and spread sample and new diluters c and d for diluting for isolation.

Figure 8D:
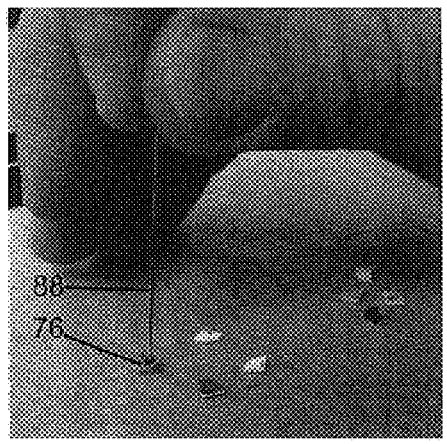
FIG. 8D illustrates a method of picking up an antimicrobial test paper for transfer to kit plate chamber.
Figure 8E:
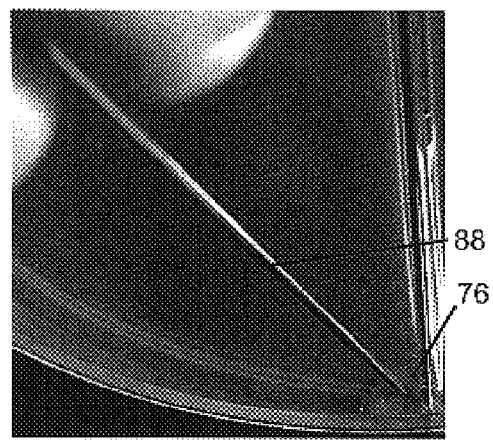
FIG. 8E illustrates the application of an antimicrobial test paper to a plate chamber corner of the invention.

Following this preparation of the kit plate, antimicrobial agent disk quarters 76 are applied to regions of the plate in order to allow antimicrobial susceptibility testing. FIG. 8D shows the method of picking up a disk quarter 76 using applicator 88. The disk quarter 76 is placed in the corner as shown in FIG. 8E. The applicator is removed from the disk quarter once placed by rotating the applicator and lifting away from the disk quarter. The "disk quarters" referred to herein are made by dividing Kirby-Bauer susceptibility testing disks into fourths. In other embodiments of the invention, other fractional portions of such Kirby-Bauer disks may be used, including full Kirby-Bauer disks. Other fractional portions, such as "disk-halves" could be used, but may increase the cost of the resulting assay.

In methods of the invention, a number of disk quarters are applied to the blood agar chamber, and a number of disk quarters are applied to the Mueller Hinton chamber. See FIG. 8F, for the addition of 14 disk quarters 76 to two AST chambers of the kit plate. In some methods of the invention, four disks are applied to each of the blood agar and Mueller Hinton agar chambers. Three of the disk quarters are placed in each of the corners of the agar chamber, and the fourth may be placed along the outside arc-shaped wall of the kit plate. A kit plate of the invention comprising the carrageenan-fortified agars of the invention and demonstrating one potential pattern for placement of the disk-fractions is shown in FIG. 5B. The antimicrobial agents subsequently diffuse from the disk quarters into the media, where they may inhibit the growth of bacteria if the bacteria are susceptible to the particular antimicrobial agent. Following placement of the disk fractions onto the kit plate, the plate may be incubated for a period of at least 12 hours. A kit plate, enclosed in packaging pouch, is shown being placed in an incubator in FIG. 8G. In some embodiments of the invention, the incubation period is from about 12 to about 24 hours.

Following incubation of the plate, observe to identify the microorganism(s) present and identify antimicrobial agents to which identified organisms are susceptible. A study of the table of colony characteristics used in the kit invention, FIG. 9, will allow the user to determine the number of different bacterial types that are on the incubated plate. In some methods of the invention, identification of bacteria on the kit and media of the invention may proceed according to methods known in the art. In other methods of the invention, bacterial identification and rather there is a significant infection or not may be determined as shown in the flow chart of FIG. 10, entitled "Post incubation analysis flow chart." Other simple tests can be performed on the colonies to determine if the gram positive organisms growing in the CCNAB media are staphylococci or streptococci using the catalase test. Staph. Is catalase positive and Strep. Catalase negative.

The gram negative colonies on the MAC can be analyzed using the cytochrome oxidase test. Several like colonies can be removed and applied to the cytochrome oxidase test paper. A positive reaction, a deep purple color produced by the colony indicates a positive test and rules out the Enterobacteriaceae family of pathogens. FIG. 11 also lists additional simple spot tests that can further differentiate gram (+) and gram (−) colonies such as the bile solubility test, the slide coagulase test, the direct spot indole test, the MUG test, and the PYR substrate test as practiced from the prior art. Following this, susceptibility of the bacteria may be determined by measuring a radius of a zone of no growth of the bacteria from an antimicrobial disk fraction. In this embodiment, the disk quarters are color coded. This radius is measured as shown in FIG. 6, and used to determine susceptibility as illustrated in FIG. 13, containing an interpretative standards table.

Generally, the larger the zone of growth inhibition, the more effective the antimicrobial agent is against the bacteria present. The zone may be measured as a radius in millimeters from the edge of the dish to the margin. The determined values may be compared with those in the table of FIG. 13, to determine whether the bacterium is resistant, intermediate, or sensitive to a specific antimicrobial agent. A more complete interpretative standards table is found in FIG. 14A and FIG. 14B. The antimicrobial disk quarter placement can be observed to be similar to a standard Kirby-Bauer AST. See FIGS. 2A and 2B.

The invention further provides kits embodying the culture and antimicrobial susceptibility testing methods of the invention. FIG. 16 illustrates an embodiment of a kit plate 30 within the scope of the invention. More specifically, FIG. 16 provides a perspective view of an embodiment of a kit plate 30 of the present invention. In this Figure, the kit plate 30 is a sterilized ethylene oxide-sterilized polypropylene multi-chambered kit plate 30 with substantially square test chambers numbered 51–75. Test chambers 67–70 and 72–75 are shown to include antimicrobial susceptibility test (hereinafter "AST") disk-fractions 76 (here disk-quarters) placed in the corners of the test chambers. These AST disk-quarters may be produced by quartering standard Kirby-Bauer AST disks using instruments such as a plastic jig and a razor blade or other methods apparent to one of ordinary skill in the art. The disk-quarters 76 may be distinguished by color, or where disk color differences are insufficient to distinguish them, the disk-quarters 76 may additionally be identified using other methods of labeling.

Figures 17, 18:
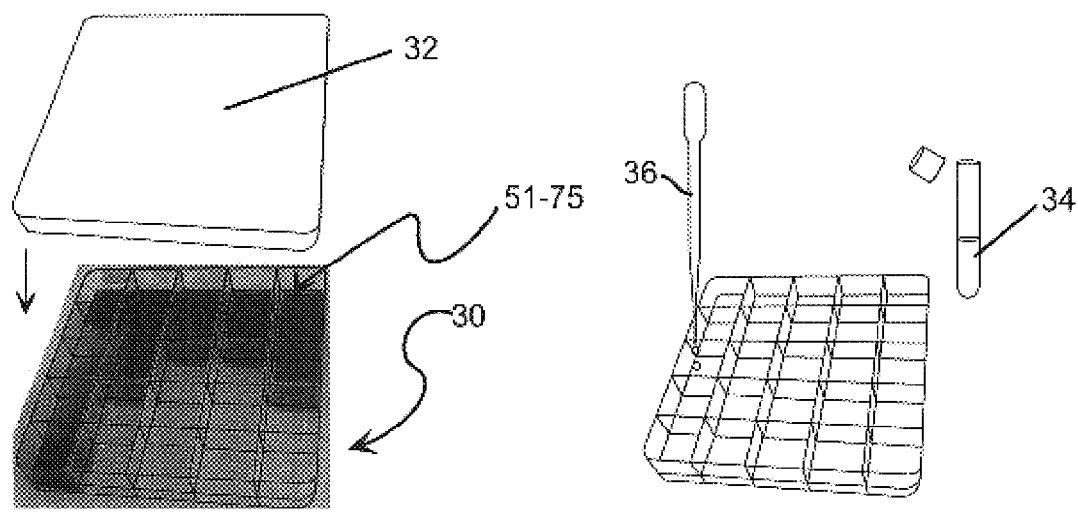
FIG. 17 shows a kit plate and lid of the invention with various selective, differential and non-selective agar-based solid carrageenan-stabilized media-placed in specific chambers.
FIG. 18 shows a method of applying microorganisms to chambers of the kit plate of FIGS. 16 and 17.

The chambers 51–76 of the test kit plate 30 may be provided with a quantity of culture media (such as an agar-based growth medium) adequate to support the growth of a microbial culture for a period of time. In some instances, the agar may be provided to a depth of 4 mm, thus occupying a volume of 1.6 milliliters and a surface area of 4 cm2. This amount may be varied to accommodate different chamber sizes, shapes, and configurations, as chamber as culture applications requiring a larger amount of medium to support growth over longer time periods. A large variety of diagnostic agar-based media may be provided in the test chambers of the kit plate 30. In the kit plate 30 illustrated in FIGS. 16 and 17, the chambers 51–75 include, respectively: Blood agar 51 (Enriched); Columbia CNA agar with blood 52 (Selective); Lactose MacConkey agar 53; Glucose MacConkey agar 54; Mannitol MacConkey agar 55; Bile esculin azide agar 56; Inositol MacConkey agar 57; Sucrose MacConkey agar 58; Arabinose MacConkey agar 59; Hektoen enteric agar 60; Mannitol salt agar 61; Simmons citrate agar 62 (Differential); *Pseudomonas* agar F 63; *Pseudomonas* agar P 64; MUG MacConkey agar 65 (Differential-Selective); Tellurite Glycine agar 66; Mueller Hinton agar 67–70; Littman oxgall agar 71; and Mueller Hinton agar 72–75. FIG. 17 shows a color view of the illustrated embodiment of the kit plate 30 taken before antimicrobial disk-quarters 76 are applied to the kit plate 30. A lid 12 is also shown for sealing the kit plate 30 once inoculated to reduce the incidence of culture of organisms found in the kit's environment instead of in the sample.

Referring next to FIG. 18, the kit plate 30 is shown ready to receive a culture dilution 34. Dilutions such as 34 may be prepared for use with the kit plate 30 using methods known to one of ordinary skill in the art Means such as a disposable sterile pipette 36 may be used to apply the dilution 34 to the kit plate 30 as shown.

As illustrated in FIG. 16, the AST disk-quarters 76 may be placed in Mueller Hinton-containing test chambers (67, 68, 69, 70, 72, 73, 74, 75) to evaluate susceptibility of the organisms present in the culture to the various antimicrobial agents.

FIGS. 13 and 16 illustrate colony and cellular morphologic properties which may be observed in bacteria growing on media. More specifically, FIG. 9 is a chart of colony properties such as form, elevation, margin, consistency, pigment, reflected and transmitted colony appearance, and colony diameter. Each colony originates from a single bacterium. There may be multiple types of bacteria or a single type of bacteria present on the plated sample. Each species of bacterial or fungal organism will exhibit a characteristic colony. A study of the morphologic differences on the plate reveals how many different species are present. FIG. 12 is a table of cellular morphology containing characteristics of microbes observed under a light microscope at 400×–600× magnification. Such information may be useful when a fuller identification of the microbes growing in culture is desired.

The test kit described in FIG. 16 includes chambers 51–75 filled with enriched, differential, selective, differential-selective and single purpose media. Common base formulations of suitable media and methods of their preparation are known in the art and available from the Eleventh edition of the Difco Manual. For use in the invention, these formulations may be modified by the addition of carrageenan, and in some embodiments, alkaline earth metal ions, to provide a more stable agar gel as taught in the parent application. According to the invention, the multi-chambered kit plate 30 and associated lid 32 may be packed under nitrogen atmosphere, or other suitable low oxygen environment into a low oxygen-permeable sealed bag to extend the shelf life of the kit 30. Another method of packing the various test kits would employ a nylon/EVOH/polyethylene pouch which provides a very low oxygen permeability. Additionally an oxygen absorber such as FreshPax oxygen absorbing packets or strips from Multisorb Technologies may be added to the pouch at time of packaging. See FIG. 4.

The process of kit plate media preparation follows standard practices of sterile technique. Envisioned but not illustrated is a process that could be used to produce the kit plates in an efficient fashion. The system conceptually would comprise a temperature-regulated box with a lid, large enough to hold the individual kit plate chamber medium vessels at a temperature of at least 50° C. The distribution of media to the test chambers 51–75 of the multi-chambered kit plate 30 or to the four chambered kit plate 210 would be accomplished by using a dispensing pump (not shown) able to dispense the correct amount of media into each test chamber 51–75. The pump would drive a multi-channeled pump head (not shown) with the same number of channels as the number of test chambers 51–75 in the kit plate 30 allowing for a relatively simple method for manufacturing the multi-chambered kit plates.

Each of the agar-based culture media used in the embodiment of the multi-chambered kit plates of the invention may be selected from the following list of media and other agar-based culture media known to those of ordinary skill in the art. Media used in the kit plates of the invention are selected in part for their individual diagnostic properties.

The blood agar provided in chamber 51 is used in the isolation of a wide variety of microorganisms. All non-fastidious gram-negative and gram-positive organisms will grow on this medium. The majority of the aerobic gram-positive and gram-negative bacterial pathogens of domestic animals and man will grow on blood agar when incubated in air at 35° C. Blood agar also allows for determination of hemolytic patterns. The hemolytic patterns adjacent to bacterial colonies are classified as non-hemolytic (gamma hemolysis), complete (beta-hemolysis), and partial (alpha-hemolytic).

The bile esculin azide agar provided in chamber 56 is used for isolating, differentiating and presumptively identifying group D *streptococcus* and *Enterococcus*. These organisms cause the formation of a dark brown or black complex in the agar.

The mannitol salt agar provided in chamber 61 allows staphylococci to grow while the growth of most other bacteria is inhibited.

The tellurite glycine agar provided in chamber 66 permits the isolation of coagulase positive staphylococci whereas coagulase negative staphylococci and other bacteria are completely inhibited. Coagulase positive staphylococci reduce tellurite and produce black colonies.

The littman oxgall agar provided in chamber 71 is used for the isolation of fungi and is suitable for growth of pathogenic fungi. Incubation is for several days. Molds and yeasts form non-spreading, discrete colonies.

The Columbia CNA agar with blood provided in chamber 52 is used in the isolation of gram-positive organisms from clinical and non-clinical specimens. The colistin and nalidixic acid in the medium suppresses the growth of gram-negative bacteria and is useful in determining hemolytic reactions.

The Simmons citrate agar provided in chamber 62 is used in the ID of gram-negative organisms that are able to metabolize citrate. The citrate-utilizing organisms grow luxuriantly and the medium becomes alkalinized and changes from its initial green to deep blue.

The *pseudomonas* agar F provided in chamber 64 is used for differentiating *Pseudomonas aeruginosa* from other pseudomonads based on fluorescein production and is visible with UV lamp at 365 nm.

The *pseudomonas* agar P provided in chamber 64 is used for differentiating *Pseudomonas aeruginosa* from other pseudomonads based on the production of pyocyanin, a non-fluorescent blue pigment.

The hektoen enteric agar provided in chamber 60 is used to isolate and differentiate *Salmonella*. Colonies are greenish blue, with black centers.

The MUG MAC provided in chamber 65 is a MacConkey agar with lactose plus an added substrate 4-methylumbelliferyl-b-D-glucuronide (MUG). MUG becomes fluorescent when *E. coli* is present. The *E. coli* beta-glucuronidase enzyme cleaves the colorless MUG to a fluorescent product detected with UV light at 365 nm.

MacConkey agar, which contains bile salts, denotes a family of selective media for culturing the majority of gram-negative pathogens. The media inhibits gram-positive bacteria and a few gram-negative pathogens. Almost 100% of the genera from the family Enterobacteriaceae (all being gram negative), and nearly 80% of other gram-negative genera grow on MacConkey agar. The following MAC media contain six different sugars to allow for ID of microorganisms based on their fermentation patterns:

The lactose MAC provided in chamber 53 is MacConkey agar with lactose, a selective and differential medium for growing gram-negative bacilli. Lactose fermenting strains grow as red or pink colonies.

The glucose MAC provided in chamber 54 is MacConkey agar with glucose, a selective and differential medium for growing gram-negative bacilli. Glucose fermenting strains grow as red or pink colonies.

The mannitol MAC provided in chamber 55 is MacConkey agar with mannitol, a selective and differential medium for growing gram-negative bacilli. Mannitol fermenting strains grow as red or pink colonies.

The inositol MAC provided in chamber 57 is MacConkey agar with inositol, a selective and differential medium for growing gram-negative bacilli. Inositol fermenting strains grow as red or pink colonies.

The sucrose MAC provided in chamber 58 is MacConkey agar with sucrose, a selective and differential medium for growing gram-negative bacilli. Sucrose fermenting strains grow as red or pink colonies.

The arabinose MAC provided in chamber 59 is MacConkey agar with arabinose, a selective and differential medium for growing gram-negative bacilli. Arabinose fermenting strains grow as red-pink colonies.

The Mueller Hinton agar provided in chambers 67–70, 72–75 is considered by many skilled in the art to be the best media for routine AST of non-fastidious bacteria. Eight test chambers are set-aside for this purpose.

Each of the above-described agar-based media and others known to those of ordinary skill in the art may be modified to include carrageenan according to the present patent application. Generally, the carrageenan is mixed with the agar while dry, and then water is added. The resulting mixture may then be heated to dissolve the components, sterilized and prepare for addition of any other components, such as azide, defibrinated sheep blood, etc.

FIGS. 2A and 2B illustrates the basic principle of the disk-diffusion method of AST. As soon as the antimicrobial agent-impregnated AST disk 78 or disk-quarter 76 is exposed to the moist agar surface, water is absorbed into the filter paper and the antimicrobial agent present in the disk 78 or disk-quarter 76 diffuses into the surrounding medium. The rate of extraction of the antimicrobial agent out of the disk 78 or disk-quarter 76 is greater than its outward diffusion into the medium, so the concentration immediately adjacent to the disk 78 or disk-fraction 76 may exceed that in the disk 78 or disk-fraction 76 itself. As the distance from the disk or disk-fraction increases, however, there is a logarithmic reduction in the antimicrobial agent concentration. If the agar based medium has been previously inoculated with a bacterial suspension, simultaneous growth of bacteria 156 occurs on the surface of the agar. When a critical cell mass of bacteria is reached, the inhibitory activity of the antimicrobial agent is overcome and microbial growth occurs. The time (critical time) required to reach the critical cell mass (4 to 10 hours for commonly tested bacteria) is characteristic of each species but is influenced by the composition of the medium and temperature of incubation. The depth of the agar will affect the lateral extent of antimicrobial diffusion before the critical time is reached because diffusion occurs in three dimensions.

The points at which the critical cell mass is reached appears as a sharply marginated circle (FIG. 2A) or arc (FIG. 2B) (margin 142), of microorganism growth. The concentration of diffused antimicrobial agent at this margin 142 of growing and non-growing bacteria is known as the critical concentration. This concentration approximates the minimal inhibitory concentration (MIC) obtained in dilution tests. The Minimal inhibitory concentration (MIC) is the lowest concentration of a chemotherapeutic agent that will prevent growth of the test microorganisms. The disk-diffusion test that has become standard in the United States is based on the work of Bauer, Kirby and coworkers. The zone size observed in a disk-diffusion test has no meaning in and of itself. The interpretative standards provided by the NCCLS show the correlation between zone sizes and MICs of those species tested by disk-diffusion method.

The method design and placement of antimicrobial agents on the AST portion of the kit plate 210 is a novel and unique modification of the standard Kirby-Bauer disk-diffusion method for AST. FIGS. 2A and 2B discussed above distinguish the prior art from an AST chamber of the kit plates 210 or 30 of the invention. One-fourth of an AST disk 78, referred to herein as a "disk-quarter" 76, is placed in the corner or along an edge of selected clambers, giving substantially the same result multiplied by 2 as the standard disk-diffusion method (inhibition radius 144×2=inhibition diameter 146). The placement of disk-quarters 76—was also discussed above.

The agar-based media of the invention differ from those known in the art in that they may be modified to incorporate carrageenan. More specifically, the media of the invention may include a carrageenan such as iota carrageenan to extend the useful shelf life of products such as kits produced using the media of the invention as discussed and claimed in the parent application. Carrageenan is a compound including mixtures of sulfated polysaccharides which are obtained as extracts of certain species of red seaweed (Rhodophyceae). Carrageenan is most commonly marketed commercially for use in food products. Commercial grades of carrageenan generally range in molecular weight from 100,000 to about 1,000,000. Carrageenan is generally sold as a powder, and is used in the production of food products, cosmetics, and pharmaceuticals. Most commonly, carrageenans are used to stabilize milk proteins and to form water gels.

Carrageenan is generally available commercially in three forms: kappa carrageenan, iota carrageenan, and lambda carrageenan. According to the invention, iota carrageenan may be used to reduce the watering out of hydrocolloid agar gels (termed "syneresis"). In addition, the incorporation of iota carrageenan into agar gels renders agar gels more stable, while increasing the shelf life of the gels produced. Further, according to the invention, the addition of ions such as potassium ions and calcium ions to the iota carrageenansupplemented agar gels of the invention may further increase the stability of the gels produced. In some embodiments of the invention, iota carrageenan is used to produce stable agar gels. In some embodiments, calcium ions are also added to the gels to further increase their stability.

Agar gels are typically prepared by suspending the agar product in cool water and then heating to boiling. The resulting solution is then allowed to cool to the hydrocolloid gel state. Agar is generally soluble in hot or boiling water. Carrageenan is similarly used by mixing first in cool water and then heating to boiling. The resulting solution is then allowed to cool to the hydrocolloid gel state. Thus, gels according to the invention may be formed by combining powdered agar and carrageenan and dissolving them together, by mixing agar and carrageenan solutions, or using other methods commonly known in the art.

Stable agar gels according to the invention include agar gels such as Mueller Hinton blood agar, Mueller Hinton agar, MacConkey agar, and Columbia CNA agar with blood which further include carrageenan. In some embodiments of the invention, the agar gels include carrageenan in an amount of less than about 1% of the solution by weight. In other embodiments of the invention, the agar gels include from about 0.1% to about 0.8% carrageenan. In still other embodiments of the invention, the agar gels include from about 0.2% to about 0.4% carrageenan. In specific embodiments, the agar gels include 0.2% carrageenan.

In still other embodiments of the invention, stable agar gels are included which incorporate carrageenan and alkaline earth metal ions such as calcium ions. In some such embodiments, the agar gels include alkaline earth metal ions at a concentration of less than about 10 mM. In other embodiments of the invention, the agar gels include from about 0.01 mM to about 1.0 mM alkaline earth metal ion. In still other embodiments of the invention, the agar gels include about 1 mM ion. In some specific embodiments of the agar gels of the invention, the agar gels include about 1 mM calcium ion.

Alternatively, the kits of the invention may instead utilize standard agar-based culture media known to those of ordinary skill in the art and found in industry references such as the Difco manual referenced supra.

The kits of the invention may also include a modified nitrate reductase determination system, a cytochrome oxidase test, a catalase test, a bile-solubility test, a slide coagulase test, a direct spot indole test, a MUG test, and a PYR substrate test known to those of ordinary skill in the art. Such will be able to perform these tests, the results of which add additional pieces of information useful in identifying organisms.

If there are more than two types of microorganisms on the kit plate, consider the following: Although polymicrobic infections do occur, particularly when mixed bacterial species are recovered from deep wounds or visceral organs, this same mixture of organisms from culture of urine, the respiratory tract, or superficial skin wounds or ulcers must be interpreted differently. R. C. Bartlett (Am. J. Clinical. Pathology 61: 867–872, 1974) has recommended that routine cultures that grow three or more organism types should not be further processed. The recovery of three or more organisms from specimens obtained from non-sterile sites most commonly represents colonization or contamination. Repeat cultures may be indicated of there is clinical evidence of infection. Others have reported similar experiences to that reported by Bartlett: that repeat cultures rarely confirm isolation of the same bacterial pathogens.

The method and kit of the invention is adaptable for the ID and AST of a broad number of microorganisms comprising gram-positive bacteria, gram-negative bacteria, higher bacteria and *Mycoplasma*, and fungi.

As another embodiment, the multi-chambered kit plate media can include several selective and differential media useful for *Bacillus*: *Bacillus cereus* selective agar (BCA) and/or Phenylethanol agar with 5% defibrinated sheep blood. Anthrax (*Bacillus anthracis*) is a large spore-forming gram-positive rod (1–1.5×3–10 micron) that forms oval, central to sub-terminal spores (1×1.5 micron) that do not cause swelling of the cell. It grows in culture as gray-white colonies, generally flat or slightly convex with characteristic comma-shaped protrusions. The edges are slightly undulate and have a ground glass appearance. Anthrax is differentiated from other gram-positive rods on culture by lack of hemolysis, lack of motility and by preferential lack of growth on Phenylethyl alcohol blood agar. Other Bacilli are generally hemolytic, motile and grow on Phenylethyl alcohol blood agar.

FIG. 16 illustrates an embodiment of one of the kit components, a multi-chambered polystyrene plate having 25 square test chambers and ethylene oxide sterilized. In other embodiments, it is possible for the kit plate to have test chambers of any number and dimension and any composition of plastic material such as polypropylene where the plastic can be formed into a multi-chambered kit plate that can be sterilized. In the case of polypropylene, the kit plate can be steam sterilized instead of ethylene oxide sterilized. Other numbers of test chambers per kit plate can be produced and utilized. In another embodiment, the kit plate may include test chambers of any geometry or shape which provides sufficient surface area for observing bacterial growth.

The table entitled "Table of Media and their Usefulness" lists additional media which may be substituted for the media used in the illustrated kit plate of the invention. Other embodiments would comprise different combinations of the medium listed below as well as newly developed formulations. Mueller Hinton medium, used in this embodiment, may be enriched with other nutrients in another embodiment. Any other suitable AST medium can be used that will allow for reliable AST. In another embodiment, an AST media can be utilized that comprises a selective agent to eliminate unimportant microorganisms, allowing only for the AST of particular pathogens. Further, as taught herein, the agar-based gels used may be stabilized by the addition of carrageenan, and in some embodiments, alkaline earth metal ions.

An embodiment where anaerobic microorganisms are AST tested would utilize a set of antimicrobial agents with clinical indications against anaerobic bacteria. Examples are Clindamycin, Imipenem, Ampicillin-Sublactam, and Metronidazole. It is important to note, concerning anaerobes, that resistance among the *B. fragilis* group is increasing, while certain *Clostridia* species are frankly resistant, and therefore AST of anaerobes is very desirable. In another embodiment, additional wells or test chambers are utilized for AST with any available antimicrobial agent under any atmosphere.

In addition to the use of different media, is the option of culturing in different gas atmospheres. These other gas environments are possible with commercial systems. Anaerobic incubators of any brand and make will suffice. A convenient alternative is the pouch systems for the anaerobic incubation of up to two of the kit plates of the invention. These systems comprise a plastic see-through pouch and a paper gas-generating sachet. The paper sachet contains ascorbic acid and activated carbon that react on contact with air. Oxygen is rapidly absorbed and carbon dioxide produced. When the paper sachet is placed in a sealed plastic pouch, the reaction creates ideal atmospheric conditions for the growth of anaerobes.

TABLE OF MEDIA AND THEIR USEFULNESS

| Medium | Usefulness |
|---|---|
| A8 agar | Isolating and differentiating genital strains of mycoplasmas. |
| Actinomycete Isolation Agar | Isolating Actinomycete from soil and water |
| Agar Medium No. F | Detecting Enterobacteriaceae and other gram-negative bacteria in pharmaceutical products |
| American Trudeau Society medium | Cultivation of acid-fast bacteria (mycobacteria) |
| Anaerobic Agar | Cultivating anaerobic microorganisms |
| Azide Blood Agar Base | Isolating streptococci and staphylococci; for use with blood in determining hemolytic reactions |
| Bacillus cereus selective agar (BCA) | Isolating and differentiating Bacillus anthracis in meat and tissue |
| Bacteroides Bile-Esculin agar | Isolation and ID of Bacteroides fragilis group and Biophilia spp. |
| BG Sulfa Agar | Isolating salmonella |
| Baird-Parker Agar Base | Isolating and enumerating staphylococci in foods and other materials |
| BIGGY Agar | Isolating and differentiating Candida spp. |
| Bile Esculin Agar Base | Isolating and presumptively identifying group D streptococci |
| Bile Esculin Agar | Isolating and presumptively identifying group D streptococci and Enterococcus spp. |
| Bile Esculin Azide Agar | Isolating, differentiating and presumptively identifying group D streptococci |
| Bismuth sulfite agar | Selective for Salmonella spp. |
| Blood agar, anaerobic (CDC) | General growth medium for anaerobic bacteria |
| Blood agar, anaer. W K & Val (CDC) | Isolation of Bacteroides spp. And other obligately anaerobic bacteria |
| Blood Agar Base | Isolating and cultivating a wide variety of microorganisms. Plus blood, fastidious organisms |
| Blood Agar Base No. 2 | Isolating and cultivating fastidious microorganisms with or without added blood |
| Blood Agar, Laked, anaerobic with K & VA | Isolation of Bacteroides spp. And other obligately anaerobic bacteria with enhanced Prevotella pigment production |
| Blood Agar, Phenylethyl alcohol, anaerobic | Isolation of Bacteroides spp., Prevotella spp., and other obligately anaerobic bacteria from facultative anaerobes. |
| Bordet Gengou Agar Base | Isolating Bordetella pertussis and other Bordetella species |
| Brain Heart Infusion Agar | Cultivating fastidious microorganisms, especially fungi and yeasts |
| Brain Heart CC Agar | Isolating and cultivating fastidious fungi |
| Brain Heart Infusion w/PAB and Agar | Cultivating fastidious organisms, particularly from blood containing sulfonamides |
| Brewer Anaerobic Agar | Cultivating anaerobic and microaerophilic bacteria |
| Brilliant Green Agar | Isolating Salmonella other than Salmonella typhi |
| Brilliant Green Agar Modified | Isolating Salmonella from water, sewage and foodstuffs |
| Brilliant Green Bile Agar | Isolating, differentiating and enumerating coliform bacteria |
| Brucella Agar | Isolating and cultivating Brucella |
| Campylobacter Agar Base | Isolating and cultivating Campylobacter |
| Candida BCG Agar Base | Isolating and differentiating Candida from primary specimens |
| Candida Isolation Agar | Isolating and differentiating Candida albicans |

-continued

TABLE OF MEDIA AND THEIR USEFULNESS

| Medium | Usefulness |
|---|---|
| Cetrimide Agar Base | Isolating and cultivating Pseudomonas aeruginosa |
| Charcoal Agar | Cultivating fastidious organisms, especially Bordetella pertussis for vaccine production |
| Chocolate Agar | Supports growth of Neisseria and Haemophilus |
| Clostridium difficile selective media | Isolating C. difficile from fecal specimens of patients |
| Columbia Blood Agar Base EH | Isolating and cultivating fastidious microorganisms when used with blood |
| Columbia Blood Agar Base | Cultivating fastidious microorganisms with or without the addition of blood |
| Columbia Blood Agar Base No. 2 | Isolating and cultivating fastidious microorganisms when used with blood |
| Columbia CNA agar w or w/o blood | A selective medium for isolation of gram-positive bacteria Antimicrobial agents, colistin and nalidixic acid, suppress Growth of gram-negative organisms. The addition of blood permits the interpretation of hemolytic activities. |
| Cooke Rose Bengal Agar | Isolating fungi from environmental and food specimens |
| Corn Meal Agar | Stimulating the production of chlamydospores by Candida albicans |
| Cystine Heart Agar | Cultivating Francisella tularensis when used with blood |
| Cystine Tryptic Agar | Used with added carbohydrates in differentiating microorganisms based on fermentation reactions |
| Czapek Solution Agar | Cultivating fungi and bacteria capable of using inorganic nitrogen |
| DCLS Agar | Isolating gram-negative enteric bacilli |
| D/E Neutralizing Agar | Used for neutralizing and determining the bactericidal activity of antiseptics and disinfectants |
| DNase Test Agar w/Methyl Green | Identify potentially pathogenic staphylococci based on deoxyribonuclease activity |
| DRBC Agar | Enumeration of yeasts and molds |
| Desoxycholate Agar | Isolating and differentiating gram-negative enteric bacilli |
| Desoxycholate Citrate Agar | Isolating enteric bacilli, particularly Salmonella and many Shigella species |
| Desoxycholate Lactose Agar | Isolating and differentiating gram-negative enteric bacilli and enumerating coliforms from water, wastewater, diary |
| Dextrose Agar | Cultivating a wide Variety of microorganisms with or without added blood |
| Dextrose Starch Agar | Cultivating pure cultures of Neisseria gonorrhoeae and other fastidious microorganisms |
| Dextrose Tryptone Agar | Cultivating thermophilic "flat-sour" microorganisms associated with food spoilage |
| Differential Reinforced Clostridial Agar | Cultivating and enumerating sulfite-reducing clostridia |
| Dubos Oleic Agar Base | Isolating and determining the susceptibility of Mycobacterium tuberculosis |
| Egg Yolk Agar | Differentiate species of anaerobic and aerobic bacteria based on detection of lecithinase, lipase, and protease activity |
| M E Agar | Isolating and differentiating enterococci from water by membrane filtration |
| Esculin Iron Agar | Enumerating enterococci from water by membrane filtration based on esculin hydrolysis |
| EMB Agar | Isolating and differentiating gram-negative enteric bacilli |
| Emerson YpSs Agar | Cultivating Allomyces and other fungi |
| Endo Agar | Confirming the presence of coliform organisms |
| M Enterococcus Agar | Isolating and enumerating enterococci in water and other materials by membrane or pour plate techniques |
| Eugon Agar | Cultivating a wide variety of microorganisms, particularly in mass cultivation procedures. |
| M FC Agar | Cultivating and enumerating fecal coliforms by membrane filter technique at elevated temperatures |
| HC Agar Base | Enumerating molds in cosmetic products |
| M HPC Agar | Enumerating heterotrophic organisms in treated potable water and other water samples by membrane filtration |
| Heart Infusion | Cultivating a wide variety of fastidious micro- |

-continued

TABLE OF MEDIA AND THEIR USEFULNESS

| Medium | Usefulness |
|---|---|
| Agar | organisms and as a base for preparing blood agar |
| Hektoen Enteric Agar | Isolating and differentiating gram-negative enteric bacilli |
| KE *Streptococcus* Agar | Isolating and enumerating fecal *streptococci* according to APHA |
| LPM Agar Base | Isolating and cultivating *Listeria monocytogenes* |
| *Lactobacilli* MRS Agar | Isolation, enumeration and cultivation of *Lactobacillus* species |
| Letheen Agar | Evaluating the bactericidal activity of quaternary ammonium compounds |
| Lima Bean Agar | Cultivating fungi |
| Littman Oxgall Agar | Isolating and cultivating fungi, especially dermatophytes |
| Liver Infusion Agar | Cultivating *Brucella* and other pathogenic organisms |
| Liver Veal Agar | Cultivating anaerobic microorganisms |
| M 17 Agar | Enumerating lactic *streptococci* in yogurt, cheese starters and other dairy products |
| MYP Agar | Enumerating *Bacillus cereus* from foods |
| MacConkey Agar | Isolating and differentiating lactose fermenting from non-fermenting gram-negative enteric *bacilli* |
| MacConkey Agar Base | Used with added carbohydrates in differentiating microorganisms based on fermentation reactions |
| MacConkey Agar CS | Isolating and differentiating gram-negative enteric *bacilli* from specimens containing swarming strains of proteus |
| MacConkey Agar w/o Salt | Isolating and differentiating gram-negative *bacilli* while suppressing the swarming of most proteus species |
| MacConkey Agar w/o CV | Isolating and differentiating enteric microorganisms while permitting growth of *staphylococci* and *enterococci* |
| MacConkey Sorbitol Agar | Isolating and differentiating enteropathogenic *E. coli* serotypes |
| Malt Agar | Isolating and cultivating yeasts and molds from food, and for cultivating yeast and mold stock cultures |
| Malt Extract Agar | Isolating, cultivating and enumerating yeasts and molds |
| Mannitol Salt Agar | Isolating and differentiating *staphylococci* |
| McBride *Listeria* Agar | Isolating *Listeria monocytogenes* with or without the addition of blood |
| McClung Toabe Agar Base | Isolating and detecting *Clostridium perfringens* in foods based on the lecithinase reaction |
| Microbial Content Test Agar | Detection of microorganisms on surfaces sanitized with quaternary ammonium compounds |
| Mueller-Hinton medium plain | Testing bacteria for susceptibility to antimicrobial agents |
| Mueller-Hinton m. with 5% sheep B. | As above with MH plain plus testing strains of *Streptococcus* spp. and other fastidious bacteria |
| Mueller-Hinton m. chocolatized | As above for MH plain, MH with 5% sheep blood plus testing *Haemophilus* and *Neisseria* |
| Mycobacteria 7H1 I Agar | Isolating, cultivating and AST testing of fastidious strains of mycobacteria |
| Milk Agar | Enumeration of microorganisms in liquid milk, ice cream, dried milk and whey |
| *Mitis Salivarius* Agar | Isolating *Streptococcus mitis, S. salivarius* and *enterococci*, particularly from grossly contaminated specimens |
| Modified Letheen Agar | Microbiological testing of cosmetics |
| Mycobiotic Agar | Isolating pathogenic fungi |
| Mycological Agar | Cultivating fungi at a neutral pH |
| Mycological Agar w/Low pH | Isolating and cultivating fungi and aciduric bacteria |
| Oatmeal Agar | Cultivating fungi, particularly for macrospore formation |
| Orange Serum Agar | Cultivating aciduric microorganisms, particularly those associated with spoilage of citrus products |
| PPLO Agar | Isolating and cultivating Mycoplasma |
| Peptone fron Agar | Detecting hydrogen sulfide production by microorganisms |
| Phenylethanol Agar | Isolating gram-positive microorganisms but markedly to completely inhibiting gram-negative microorganisms |

-continued

TABLE OF MEDIA AND THEIR USEFULNESS

| Medium | Usefulness |
|---|---|
| Phenylalanine Agar | Differentiating *Proteus* and *Providencia* species from other *Enterobacteriaceae* based on deamination of phenylalanine |
| Potato Dextrose Agar | Culturing yeasts and molds from food and dairy products |
| Protease No. 3 Agar | Isolating and cultivating *Neisseria* and *Haemophilus* |
| *Pseudomonas* Agar F | Detecting the production of fluorescein. Produced by *P. seruginosa, P. putida, P. fluorescens* and unidentified fluor. *P.* |
| *Pseudomonas* Agar P | Detecting and differentiating *Pseudomonas aeruginosa* from other *pseudomonas* based on pyocyanin production |
| *Pseudomonas* Isolation Agar | Isolating *Pseudomonas* and differentiating *Pseudomonas aeruginosa* from other pseudomonads based on pigment |
| Rice Extract Agar | Differentiating *Candida albicans* and other *Candida* spp. based on chlamydospore formation |
| Rose Bengal Agar Base | Isolating and enumerating yeasts and molds |
| SABHI Agar Base | Isolating and cultivating pathogenic fungi |
| SPS Agar | Detecting and enumerating *Clostridium perfringens* in food |
| Sabouraud Dextrose Agar | Culturing yeasts, molds and aciduric microorganisms |
| *Salmonella-Shigella* Agar | Isolation of *Salmonella* spp. And many strains of *Shigella* spp. from feces |
| Sabouraud Maltose Agar | Culturing yeasts, molds and aciduric microorganisms |
| Simmons Citrate Agar | Differentiation of enteric gram-negative *bacilli* from clinical specimens, water samples, and food samples |
| Spirit Blue Agar | Detecting and enumerating lipolytic microorganisms in diary products |
| TCBS Agar | Isolating and cultivating *Vibrio cholerae* and other enteropathogenic vibrios |
| M TEC Agar | Isolating, differentiating and enumerating thermotolerant *E. coli* from water by membrane filtration |
| TPEY Agar Base | Detecting and enumerating coagulase-positive *staphylococci* |
| Tellurite Glycine Agar | Isolating coagulase-positive *staphylococci* |
| *Thermoacidurans* Agar | Isolating and cultivating *Bacillus coagulans* (*Bacillus thermoacidurans*) from foods |
| Thiosulfate citrate bile salts sucrose agar | Isolating *Vibrio cholerae* and other pathogenic vibrios from samples of feces and food containing mixed species |
| Tomato Juice Agar | Cultivating and enumerating *Lactobacillus* species |
| Tomato Juice Agar Special | Cultivating and enumerating *lactobacilli* and other acidophilic microorganisms from saliva and other specimens |
| Triple Sugar Iron Agar | Differentiating gram-negative enteric *bacilli* based on fermentation of dextrose, lactose, sucrose and on H2S production |
| Tryptic Soy Agar | Isolating and cultivating fastidious microorganisms and, with blood, in determining hemolytic reactions |
| Tryptone Glucose Extract Agar | Cultivating and enumerating microorganisms in water and dairy products |
| Tryptose Agar | Isolation of *Brucella* from blood |
| Tryptose Blood Agar Base | Isolating, cultivating and determining the hemolytic reactions of fastidious microorganisms |
| VJ Agar | Isolating coagulase-positive, mannitol-fermenting *staphylococci* |
| Veal Infusion Agar | Cultivating fastidious microorganisms with or without the addition of blood |
| *Veillonella* Agar | Isolating *Veillonella* when used with vancomycin |
| Violet Red Bile Agar | Enumerating coliform organisms in dairy products |
| Violet Red Bile. Agar with MUG | Enumerating *E. coli* and total coliform bacteria in food and dairy products |
| Violet Red Bile Glucose Agar | Detecting and enumerating *Enterobacteriaceae* in food and dairy products |
| XLD Agar | Isolating and differentiating gram-negative enteric *bacilli*, especially *Shigella* and *Providencia* |

-continued

TABLE OF MEDIA AND THEIR USEFULNESS

| Medium | Usefulness |
| --- | --- |
| XLT4 Agar Base | Isolating non-typhi *Salmonella* |
| YM Agar | Cultivating yeasts, molds and other aciduric microorganisms |
| Yeast Extract Glucose Chloramphenicol Agar | Enumerating yeasts and molds in milk and milk products (recommended by International dairy Federation) |
| *Yersinia* Selective Agar Base | Isolating and cultivating *Yersinia enterocolitica* |

According to another embodiment of the invention, the kits, agar media, and methods of the invention may be adapted for use with urine samples. More specifically, the kits, media, and methods taught above may be adapted for use in the diagnosis and antimicrobial susceptibility testing of bacteriuria. Bacteriuria is often observed in patients afflicted with urethritis, cystitis, and pyelonephritis. Ordinarily, urine is tested in a multi-step process. In this process, a urine sample (preferably a "clean catch" collected midstream from a urine flow) is first examined for the presence of red and white blood cells and bacteria. When bacteria are discovered, they are cultured and next subjected to testing against a variety of antimicrobial agents to determine the drug best suited to treat the particular infection.

Bacterial infections may be treated using a wide variety of suitable antimicrobial agents. The choice of antimicrobial agent and the duration of the treatment recommended directly depend on the bacteria identified, as well as upon the history of the individual patient. Antimicrobial susceptibility testing of the identified bacteria is very helpful to a physician in making this determination. Drugs often prescribed in such situations include, but are not limited to, trimethoprim (trimpex), trimethoprim/sulfamethoxazole (Bactrim, Septra, CA), amoxicillin (Amoxil, Trimox, Wymox), nitrofurantoin (Macrodantin, Furadantin), and ampicillin. Quinolone-based drugs have also been approved for the treatment of infections of the urinary tract. These include ofloxacin (Floxin), norfloxacin (Noroxin), ciprofloxacin (Cipro), and trovafloxin (Trovan).

As with other bacterial infections, although the majority of symptoms are relieved and the large majority of organisms are destroyed by a couple of days of treatment, a longer course is generally prescribed to assure complete curing of the infection and thus prevent the bacteria from developing resistance to the prescribed drug.

According to the invention, a quantitative analysis of bacteriuria may be completed with concurrent direct antimicrobial susceptibility testing in 12–18 hours. In this testing, up to about 14 antimicrobial agents may be tested, and individual colonies may be isolated for subsequent testing if later desired.

According to these methods of the invention for testing urine, a urine sample is first collected. It is generally preferable for the urine sample to be collected using a "clean catch" method as briefly described above and known to one of ordinary skill in the art. Following gathering of the urine sample in a sterile container, a small quantity of the sample is applied to each chamber of a testing kit provided according to the invention.

In one family of embodiments of the invention, a testing kit is provided that includes four chambers. Such a kit may comprise a Petri dish divided into quarters, as is illustrated in FIG. 5A. Each chamber of the kit is provided with a specific type of agar. The agar media used may be stabilized using carrageenan as taught above. In the embodiment of the invention illustrated in FIG. 5A, the kit includes four chambers. Two of the chambers were provided individually with Mueller-Hinton agar with and without blood. A third chamber was provided with MacConkey agar, and a fourth with CCNA agar. Each Mueller-Hinton agar chamber was inoculated with 20 micro-liters of the sample, with the sample being evenly distributed across the surface of the medium.

One method of applying the sample to the Mueller-Hinton agar chambers includes the steps of utilizing a 10 micro-liter calibrated loop bent at an angle. One method of assuring even distribution of the sample over the surface of the medium is illustrated in FIG. 8B, in which the sample is spread in at least three different orientations evenly across the surface to help assure even distribution.

Following application of sample to the Mueller-Hinton chambers, sample is applied to the MAC and CCNA chambers. Methods of application to these chambers are illustrated in FIG. 8C, respectively. These methods involve transferring approximately about 10 micro-liters of sample to a corner of each chamber, and diluting the sample using diluter loops bent at an angle. The samples are diluted by streaking them first in one direction with a diluter 86 approximately perpendicular to the corner, and then streaking it again with a new diluter 86 in a second direction approximately perpendicular to the first direction. This provides for the growth of isolated bacterial colonies.

Figure 8F:
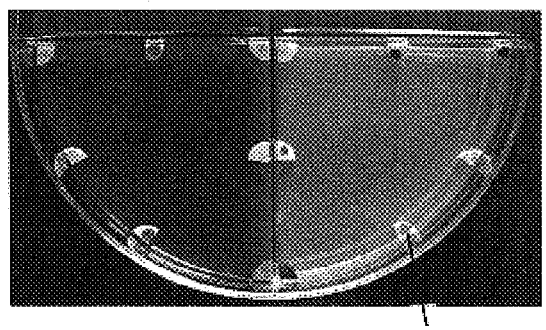
FIG. 8F shows a portion of a kit plate of the invention and various suitable patterns illustrating the placement of a larger number of Kirby-Bauer disk-fractions according to some of the methods of the invention.
Figure 8G:
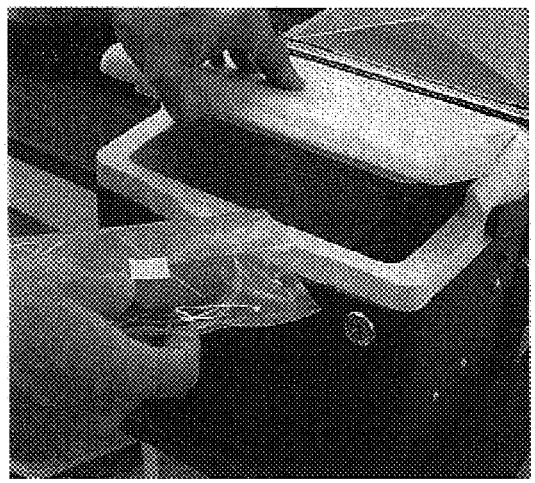
FIG. 8G shows a photograph of a kit plate of the invention, enclosed in a pouch, being placed in an incubator

To allow antimicrobial susceptibility testing of the organisms cultured in the kit of the invention, test disk-quarters may be applied to the Mueller-Hinton agar chambers as illustrated in FIG. 5B. Patterns for arranging the diskquarters in the two Mueller-Hinton chambers to allow for the testing of from 8 up to about 14 individual antimicrobial agents are shown in FIG. 8F. These placements may be varied widely within the scope of the invention. In addition to those examples illustrated in FIG. 8F, it is understood that fewer than eight antimicrobial agents may be placed in either or both of the Mueller-Hinton chambers. Instructions for the use of each of the agents may be provided in instructions provided for the kit. Each of the antimicrobial disk-quarters may be color-coded, numbered, or otherwise classified for easy identification and use by a user of the kit.

In practice, an applicator 88, illustrated in FIG. 7 may be provided in the kits of the invention to aid a user in placing the antimicrobial papers. In use, the applicator illustrated in FIGS. 8D and 8E may be used to pick up and apply the papers to the two Mueller-Hinton chambers. This may be done by gently stabbing the papers and then placing them in their intended position. When placing the papers in corners of the chamber, the flat edges may be placed so as to be adjacent to or touch the edges of the kit. The applicator may be separated from the paper by gently rotating the applicator and lifting it away from the paper. Papers placed along the arc or flat edges of the chambers of the kit may be applied with a flat edge against the edges of the chamber. Other suitable application mechanisms are discussed supra.

Following placement of the antimicrobial papers, in some methods according to the invention, it is beneficial to seat the papers against the surface of the agar medium. This may be done by gently pressing the papers against the surface without pressing them into the medium. One example of a kit according to the invention including fourteen antimicrobial papers properly applied is illustrated in FIG. 8F.

Following these steps, the inoculated kit with antimicrobial papers is prepared for incubation. A lid 211 or other covering may be placed over the kit to prevent contamination or drying out of the sample. The kit may additionally be placed in a package such as its original packaging to further protect it. This packaging may further be sealed. The kit may then be incubated at approximately about 35 degrees C. for from about 12 to about 18 hours. Following incubation of the kit, observations may be made to determine some basic classifying information regarding any bacteria cultured on the kit, the concentration of the bacteria, and the antimicrobial susceptibility of the organisms cultured.

Referring to the flowchart of FIG. 10, a method is presented for analyzing the kit following incubation. In a first step, the kit is visually evaluated for the presence of bacterial colonies. If no bacterial colonies are found, then it is most likely that no bacterial infection is present or that the infection is an anaerobic one If, however, bacterial colonies are present, FIG. 9 assists the user in determining how many of each of the different types of colonies are present on the kit plate. Non-significant infection is apparent if generally more than two types of colonies are present or there is an absence of a predominant species (10 times the number of any other type of colony) or no growth. A significant infection exists if generally only one type of colony is present or a predominant number of one colony type is found. If the specimen is a urine sample, the concentration of the bacteria is determined. This concentration is measured in colony forming units per milliliter of sample and is determined by counting the number of colonies within a single square centimeter of either Mueller-Hinton chamber of the kit. It is generally best practice to select a region of the selected Mueller-Hinton chamber that is away from any antimicrobial susceptibility testing papers. The number obtained is then multiplied by the surface area of the chamber, which is, in the case of the embodiment illustrated in FIG. 5A, 15 cm$^2$. This result is then divided by 0.02 ml, which is the initial volume of sample added. This provides a result measured in colony-forming units per milliliter. The characteristics of the observed colonies are also noted in order to determine whether the bacteria cultured are of a single type or if they are of multiple types.

Growth on the Columbia CNA plate indicates the presence of gram positive bacteria. These generally include staphylococci, streptococci, and enterococci, as well as yeasts. Growth on the MacConkey agar indicates the presence of Gram negative bacteria.

At this point, if antimicrobial papers were applied to the kit following application of the sample to the kit, a user can examine the kit to determine the antimicrobial susceptibility of organisms present in the sample. As discussed briefly above, following application of the sample to the kit, antimicrobial papers may be placed in various positions on the Mueller-Hinton chambers of the kit. Antimicrobial agents present in the papers then leach out into the culture medium. The diffusion of these agents through the medium creates a concentration gradient of each agent extending away from the test paper. In this gradient, the concentration of the antimicrobial agent gradually decreases with distance away from the antimicrobial paper, with the strongest concentration of agent being present at the paper itself.

With each agent, there is a specific distance at which the concentration of antimicrobial agent diffused into the medium is insufficient to inhibit microbial growth. This is illustrated in FIGS. 2A and 2B discussed above, which feature diagrams of a portion of a kit according to the invention. This distance presents itself as an arc, about the test paper. This arc is referred to as the "margin" and is illustrated in FIG. 2B, denoted by reference number 142. This margin 142 defines a zone 140 of no bacterial growth within, and an area 156 of growing bacteria without. In some cases, a given antimicrobial agent may have no effect on the organisms growing on the plate—in such an event, the colonies may grow right up to the specific antimicrobial paper. The ability of a specific agent to inhibit microbial growth can be measured by measuring the radius 144 of the margin 142 present around the specific antimicrobial paper.

This radius 144 is measured from a corner of the chamber if the antimicrobial disk-quarter was placed in a corner of the chamber. If the antimicrobial disk-quarter is placed along a wall of the kit, the measurement is made from the inner wall of the chamber to the margin 142. This value may be either measured in or converted to millimeters for use with the interpretive table provided in FIG. 13. The table of FIG. 17: describes a set of specific antimicrobial agents that are used in some embodiments of the testing kits of the invention. In this embodiment, the antimicrobial agents tested were ampicillin, amoxicillin/clavulanic acid, cephalothin, ciprofloxacin, doxycycline, erythromycin, levofloxacin, trimethoprim/sulfamethoxazole, and nitrofurantoin.

For each of these, the table provides ranges of margin radii 144 correlating with the presence of microbes that are either resistant, intermediately resistant, or susceptible to the action of each agent. Many other combinations of antimicrobial agents can be used as listed in a more complete zone interpretive chart as shown in FIGS. 14A and 14B. Some agents are broad spectrum and are effective against both gram negative and gram positive organisms ("mac or ccna") or are specific for gram positive ("ccna") or gram negative ("mac"). The list comprises the following antimicrobial agents: amdinocillin, amikacin, amoxicillin/clavulanic acid, ampicillin, ampicillin/sulbactam, azithromycin, azlocillin, aztreonam, bacitracin, carbenicillin, cefaclor, cefamandole, cefazolin, cefdinir, cefepime, cefixime, cefmetazole, cefonicid, cefoperazone, cefotaxime, cefotaxime/clavulanic acid, cefotetan, cefoxitin, cefpodoxime, cefprozil, ceftazidime, ceftazidime/clavulanic acid, ceftibuten, ceftizoxime, ceftriaxone, cefuroxime, cephalothin, chloramphenicol, cinoxacin, ciprofloxacin, clarithromycin, clindamycin, colistin, doxycycline, enoxacin, erythromycin, fosfomycin, furazolidone, gatifloxacin, gentamicin, grepafloxacin, imipenem, kanamycin, levofloxacin, lincomycin, linezolid, lomefloxacin, loracarbef, meropenem, methicillin, mezlocillin, minocycline, moxalactam, moxifloxacin, nafcillin, nalidixic acid, neomycin, netilmicin, nitrofurantoin, nitrofurazone, norfloxacin, novobiocin, ofloxacin, oxacillin, oxolinic acid, oxytetracycline, penicillin, piperacillin, piperacillin/tazobactam, polymyxin B, quinupristin/dalfopristin, rifampin, sparfloxacin, spectinomycin, streptomycin, sulfachloropyridazone, sulfadiazine, sulfamethizole, sulfathiazole, sulfisoxazole, tetracycline, ticarcillin, ticarcillin/clavulanic acid, tobramycin, trimethoprim, trimethoprim/sulfamethoxazole, triple sulfa, trovafloxacin, vancomycin, Enrofloxicin (veterinary), marbofloxicin (veterinary).

SUMMARY

The methods and kits described herein provide a novel and unique diagnostic tool for the characterization of unknown microorganisms from any source. The advantages take on significant meaning in a world where the unseen microscopic enemy either conquers or is conquered. The outcome depends on the readiness of the body's defense system to fight the pathogen plus how quickly the organism is identified, susceptibility tested and treatment started. The sooner the administration of the right antimicrobial agent, the better the chance is for winning the battle.

The kits of the invention may yield results (concurrent ID and AST) in as little as one-third the time of standard methods, usually within 24 hours. This may provide a critical advantage in situations of life-threatening illnesses where it is important to know which antimicrobial agent to use as well as the identity of the pathogen. Further, the kits may be constructed in such a manner as to be cost effective and may be complete such that no additional items are needed to implement or use them.

According to the methods of the invention, the specimen may be directly inoculated into the kit with no delay in transporting the specimen. (There are a number of bacteria that will not survive transport, such as *streptococcus pneumonia*, when placed in prior art transport systems.) The antimicrobial portion (AST) shows visible results even by 8 hours, with the faster growing Enterobacteriaceae family of microorganisms. The kit may be used anywhere that an incubation temperature can be maintained (35° C.–37° C.). The kit is versatile in that many different types of organisms may be tested. Since there is no initial isolation step, there is a reduced likelihood of errors in judgment and results are obtained quickly.

The AST portion of the kit is also novel and unique in that the end-of-incubation measurements correlate exactly (×½) to the standard Kirby-Bauer disk-diffusion AST system. Any set of antimicrobial agents can be tested and more than one microorganism can exist in the same test chamber and still be analyzed (see above). Finally, the stabilized agar media formulations of the invention provide kits having an extended shelf life and increased reliability due to a significant reduction in syneresis.

A paradigm in microbiology is that isolated colonies are required (i.e. "pure cultures") before any identification testing can begin. Streak plates are prepared and incubated for that purpose. Eighteen to 24 hours later, the colonies that form are tested by picking them from the plate and transferring for additional growth (18–24 hours) in identification systems or ID media. When the ID is established, an additional 18–24 hours are required to do AST for each microorganism deemed important. Another paradigm states that to do an AST test it is again required to first isolate the organism(s) of interest. The present method and kit allows for a significant short cut with no sacrifice to reliability. The present method incorporates a direct antimicrobial susceptibility test that has previously been shown to be reliable and fast. Isolations and identifications of several microorganism types take place together in the same chambers at the same time without the need for an initial 18 to 24 hours isolation step first. In the four chambered kit plates, there are specific isolation methods performed on the gram (+) and gram (−) selective media. This is useful where further identification is desired. In certain cases, selective or single purpose media will perform the "isolating", because only one type of organism will grow on a particular medium. Two examples are the ID of *Enterococcus* on Bile Esculin Azide agar or the ID of Coagulase-positive *staphylococcus* on Tellurite Glycine agar. Reliable ID and AST, using the novel kit and method, may be conducted with a direct culture.

Many potential variations of the agar, kits, and methods of the invention are possible within the scope of the invention. Some variations of a number of the elements of the present kit and method are listed below. The inoculation of the culture can be done by using any number of different elements besides a loop 84 or dropper 36. For instance, a syringe and needle serves this purpose as well as any other device that will sample the point of interest containing the microorganism for study. The type of incubation vessel can be any number of different materials. The culture atmosphere can comprise any type and mixture of gas. The way of determining and preparing the density of the bacterial growth for study can be by any number of methods from the McFarland standards to a spectrophotometric determination. The method of inoculating the multi-chambered kit plate can also be different than that shown in the illustrations and described above, as known to one of skill in the art. Suitable methods may likely range from using a multi-pipette to spraying the inoculum onto the kit plate. Any that will allow for the even distribution of inoculum is permissible. Other chemistries that would elucidate the identification of an unknown microorganism from the unique colony of the organism such as newer methods of molecular biology would be permissible such as PCR, immunological methods or other methods heretofore undiscovered to assay the composition of the cellular DNA, antigenic nature, or other molecular features of the specific microorganism.

One embodiment of the kit Includes reagents and analytical papers for the determination of catalase activity, nitrate reductase, and cytochrome oxidase activity, a bile solubility test, a slide coagulase test, a direct spot indole test, a MUG test, and a PYR substrate test on the microorganisms growing from the specimen. However, other reagents in various forms can be utilized in the method. Other embodiments could utilize discs or similar material impregnated with various enzyme substrates, carbohydrates, or with various chemical agents for differentiating microorganisms on the identification section of the kit plate. Each of these differentiation discs may be used for presumptive identification of specific organisms. The carbohydrate discs are for the differentiation of microorganisms based on carbohydrate fermentation patterns. In addition, an anaerobe differentiation disc set may be used in the presumptive identification of gram-negative anaerobic bacilli.

Databases can be developed for searching gram-positive microorganisms as is shown for gram-negative microorganisms in the kit and method. It is possible to generate a set of criteria from the kit results for these and other types of microorganisms. In addition, it is practical to generate additional criteria using additional methods of biochemistry for more definitive identification.

The process of preserving the kit plates for later use comprise the packaging and storage under a nitrogen atmosphere performed in a glove box in a low permeability bag. Other embodiments would be to package under nitrogen in a Mylar-foil bag for complete protection against oxygen. Another inert gas could be used to package the kit plates also with another type of impermeable bag or container. Another method of packing the various test kits would employ a nylon/EVOH/polyethylene pouch which provides very low oxygen permeability. Additionally an oxygen absorber such as FreshPax oxygen absorbing packets or strip may be added to the pouch at time of packaging. See FIG. 4.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method of antimicrobial-susceptibility testing microbes present in a sample, the method comprising the steps of:
   applying a portion of the sample containing microbes to a culture plate containing agar-based media;
   applying a fraction of an antimicrobial susceptibility test disk to the culture plate such that the fraction abuts at least one wall of the plate, wherein the fraction is approximately one quarter or one half of the test disk and the flat edge of the quarter disk or the half disk abuts a wall of the plate or the flat edges of the quarter disk abut adjacent corner walls of the plate;
   incubating the culture plate;
   determining the presence of a zone of inhibition about the fraction of the antimicrobial test disk;
   measuring a radius of the zone of inhibition and multiplying the radius by a factor of two to obtain an inhibition diameter value; and
   comparing the inhibition diameter value obtained with standardized disk diffusion antimicrobial-susceptibility interpretation charts to provide antimicrobial-susceptibility information about the sample.

2. The method of claim 1, wherein the antimicrobial susceptibility information obtained from the method is substantially identical to antimicrobial susceptibility information obtained using a standardized antimicrobial susceptibility testing disk diffusion method that utilizes full-size antimicrobial susceptibility test disks.

3. The method of claim 1, wherein the test disk contains an antimicrobial agent selected from the group consisting of: amdinocillin, amikacin, amoxicillin/clavulanic acid, ampicillin, ampicillin/sulbactam, azithromycin, azlocillin, aztreonam, bacitracin, carbenicillin, cefaclor, cefamandole, cefazolin, cefdinir, cefepime, cefixime, cefmetazole, cefonicid, cefoperazone, cefotaxime, cefotaxime/clavulanic acid, cefotetan, cefoxitin, cefpodoxime, cefprozil, ceftazidime, ceftazidime/clavulanic acid, ceftibuten, ceftizoxime, ceftriaxone, cefuroxime, cephalothin, chloramphenicol, cinoxacin, ciprofloxacin, clarithromycin, clindamycin, colistin, doxycycline, enoxacin, erythromycin fosfomycin, furazolidone, gatifloxacin, gentamicin, grepafloxacin, imipenem, kanamycin, levofloxacin, lincomycin, linezolid, lomefloxacin, loracarbef, meropenem, methicillin, mezlocillin, minocycline, moxalactam, moxifloxacin, nafcillin, nalidixic acid, neomycin, netilmicin, nitrofurantoin, nitrofurazone, norfloxacin, novobiocin, ofloxacin, oxacillin, oxolinic acid, oxytetracycline, penicillin, piperacillin, piperacillin/tazobactam, polymyxin B, quinupristin/dalfopristin, rifampin, sparfloxacin, spectinomycin, streptomycin, sulfachloropyridazone, sulfadiazine, sulfamethizole, sulfathiazole, sulfisoxazole, tetracycline, ticarcillin, ticarcillin/clavulanic acid, tobramycin, trimethoprim, trimethoprim/sulfamethoxazole, triple sulfa, trovafloxacin, vancomycin, enrofloxicin, and marbofloxicin.

4. A method of simultaneously identifying and antimicrobial-susceptibility testing microbial species presentwithin a sample, the method comprising the steps of:
   applying a portion of the sample to a first chamber of a multi-chambered microbial culture plate, the chamber comprising a agar-based medium selective for growth of gram positive microbes;
   streaking the portion of the sample in the first chamber to dilute it and promote isolation of individual gram positive microbial colonies for identification;
   applying a portion of the sample to a second chamber of the culture plate, the second chamber comprising a selective for growth of gram negative microbes;
   streaking the portion of the sample in the first chamber to dilute it and promote isolation of individual gram negative microbial colonies for identification agar-based medium;
   applying and uniformly spreading a portion of the sample to a third chamber of the culture plate, the third chamber comprising an enriched agar based medium;
   applying a fraction obtained from each of a plurality of antimicrobial susceptibility test disks containing different antimicrobial agents to the third chamber of the culture plate such that said fractions abut at least one wall of the plate wherein the fractions are approximately one quarter or one half of the test disks and the flat edge of the quarter disks or the half disks abuts a wall of the plate or the flat edges of the quarter disks abut adjacent corner walls of the plate;
   incubating the culture plate;
   ascertaining the number of different colony types that are present in the first and second chamber based on colony characteristics;
   ascertaining if the colonies are gram positive or gram negative;
   ascertaining the presence of zones of inhibition about the fractions of the antimicrobial test disks;
   measuring radii of the zones of inhibition and multiplying each radius by a factor of two to obtain zone inhibition diameter values; and
   comparing the zone inhibition diameter values to values published in a zone diameter interpretive chart to provide antimicrobial-susceptibility information about the microbial species present within the sample.

5. The method of claim 4, wherein selective agar-based medium of the first chamber is selected from the group consisting azide blood agar, CCNA agar with or without blood, phenylethanol agar with or without blood, manitol salt agar, and bile esculin azide agar.

6. The method of claim 4, wherein the selective agar-based medium of the second chamber is selected from the group consisting of: lactose MacConkey agar, glucose MacConkey agar, mannitol MacConkey agar, inositol MacConkey agar, sucrose MacConkey agar, arabinose MacConkey agar, hektoen enteric agar, and EMB agar.

7. The method of claim 4, wherein the enriched non-selective agar-based medium of the third chamber is a non-selective agar-based medium selected from the group consisting of blood agar, chocolatized blood agar, Mueller-Hinton agar with or without blood.

8. The method of claim 4, wherein the antimicrobial susceptibility information obtained from the method is substantially identical to antimicrobial susceptibility information obtained using a standardized antimicrobial susceptibility testing disk diffusion method that utilizes full-size antimicrobial susceptibility test disks.

9. The method of claim 4, wherein the test disks contain an antimicrobial agent selected from the group consisting of: amdinocillin, amikacin, amoxicillin/clavulanic acid, ampicillin, ampicillin/sulbactam, azithromycin, azlocillin, aztreonam, bacitracin, carbenicillin, cefaclor, cefamandole, cefazolin, cefdinir, cefepime, cefixime, cefmetazole, cefonicid, cefoperazone, cefotaxime, cefotaxime/clavulanic acid, cefotetan, cefoxitin, cefpodoxime, cefprozil, ceftazidime, ceftazidime/clavulanic acid, ceftibuten, ceftizoxime, ceftriaxone, cefuroxime, cephalothin, chloramphenicol, cinoxacin, ciprofloxacin, clarithromycin, clindamycin, colistin, doxycycline, enoxacin, erythromycin, fosfomycin, furazolidone, gatifloxacin, gentamicin, grepafloxacin, imipenem, kanamycin, levofloxacin, lincomycin, linezolid, lomefloxacin, loracarbef, meropenem, methicillin, mezlocillin, minocycline, moxalactam, moxifloxacin, nafcillin, nalidixic acid, neomycin, netilmicin, nitrofurantoin, nitrofurazone, norfloxacin, novobiocin, ofloxacin, oxacillin, oxolinic acid, oxytetracycline, penicillin, piperacillin, piperacillin/tazobactam, polymyxin B, quinupristin/dalfopristin, rifampin, sparfloxacin, spectinomycin, streptomycin, sulfachloropyridazone, sulfadiazine, sulfamethizole, sulfathiazole, sulfisoxazole, tetracycline, ticarcillin, ticarcillin/clavulanic acid, tobramycin, trimethoprim, trimethoprim/sulfamethoxazole, triple sulfa, trovafloxacin, vancomycin, enrofloxicin, and marbofloxicin.

10. The method of claim 4, further comprising the steps of:

applying and uniformly spreading a portion of the sample to a fourth chamber of the culture plate, the fourth chamber comprising an enriched agar-based medium; and applying a fraction obtained from each of a plurality of antimicrobial susceptibility test disks containing different antimicrobial agents to the fourth chamber of the culture plate such that the fractions abut at least one wall of the plate, wherein the fractions are approximately one quarter or one half of the test disks and the flat edge of the quarter disks or the half disks abuts a wall of the plate or the flat edges of the quarter disks abut adjacent corner walls of the plate.

11. The method of claim 10, wherein the enriched agar-based medium of the fourth chamber is a non-selective agar-based medium selected from the group consisting of blood agar, chocolatized blood agar, and Mueller-Hinton agar with or without blood.

* * * * *